United States Patent
Moszner et al.

(10) Patent No.: US 11,998,621 B2
(45) Date of Patent: Jun. 4, 2024

(54) TRANSPARENT, FRACTURE-TOUGH POLYMERIZATION RESINS FOR THE PRODUCTION OF DENTAL SHAPED BODIES

(71) Applicant: Ivoclar Vivadent AG, Schaan (LI)

(72) Inventors: Norbert Moszner, Triesen (LI); Jörg Angermann, Sargans (CH); Iris Lamparth, Grabs (CH); Yohann Catel, Sevelen (CH); Kai Rist, Feldkirch (AT)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 17/736,166

(22) Filed: May 4, 2022

(65) Prior Publication Data

US 2022/0370300 A1    Nov. 24, 2022

(30) Foreign Application Priority Data

May 7, 2021   (EP) ................... 21172707

(51) Int. Cl.
| | | |
|---|---|---|
| *B33Y 70/00* | (2020.01) | |
| *A61C 9/00* | (2006.01) | |
| *A61C 13/34* | (2006.01) | |
| *A61K 6/15* | (2020.01) | |
| *A61K 6/62* | (2020.01) | |
| *A61K 6/889* | (2020.01) | |
| *A61K 6/893* | (2020.01) | |
| *B29C 64/386* | (2017.01) | |
| *B33Y 10/00* | (2015.01) | |
| *B33Y 50/00* | (2015.01) | |
| *C08L 51/08* | (2006.01) | |
| *B29K 96/04* | (2006.01) | |
| *B29K 105/00* | (2006.01) | |
| *B29L 31/00* | (2006.01) | |

(52) U.S. Cl.
CPC .............. *A61K 6/889* (2020.01); *A61C 9/004* (2013.01); *A61C 13/34* (2013.01); *A61K 6/15* (2020.01); *A61K 6/62* (2020.01); *A61K 6/893* (2020.01); *B29C 64/386* (2017.08); *B33Y 10/00* (2014.12); *B33Y 50/00* (2014.12); *B33Y 70/00* (2014.12); *C08L 51/08* (2013.01); *B29K 2096/04* (2013.01); *B29K 2105/0085* (2013.01); *B29L 2031/753* (2013.01)

(58) Field of Classification Search
None
See application file for complete search history.

(56) References Cited

U.S. PATENT DOCUMENTS

| | | | |
|---|---|---|---|
| 6,063,830 A * | 5/2000 | Deguchi | A61K 6/893 |
| | | | 524/534 |
| 9,333,148 B2 | 5/2016 | Suzuki | |
| 9,795,541 B2 | 10/2017 | Fontein et al. | |
| 10,299,896 B2 | 5/2019 | Sun et al. | |
| 10,562,995 B2 | 2/2020 | Sakamaki et al. | |
| 10,568,814 B2 | 2/2020 | Lee | |
| 10,588,725 B2 | 3/2020 | Hagiwara et al. | |
| 10,973,742 B2 | 4/2021 | Sakamaki et al. | |
| 2012/0196952 A1* | 8/2012 | Suzuki | A61K 6/887 |
| | | | 523/105 |
| 2014/0131908 A1 | 5/2014 | Sun et al. | |
| 2017/0333167 A1* | 11/2017 | Hagiwara | A61C 13/087 |
| 2018/0000570 A1 | 1/2018 | Sun et al. | |
| 2019/0053883 A1 | 2/2019 | Sun et al. | |

FOREIGN PATENT DOCUMENTS

| | | | |
|---|---|---|---|
| EP | 3564206 A1 * | 11/2019 | |
| EP | 3564206 A1 | 11/2019 | |
| EP | 3564282 A1 | 11/2019 | |

OTHER PUBLICATIONS

Viohl, J. et al., "The chemistry of dental filling plastics," Carl Hanser Verlag, Munich Vienna, 1986, 8 pages.
Moszner, Norbert, et al., "New Polymer-Chemical Developments in Clinical Dental Polymer Materials: Enamel-Dentin Adhesives and Restorative Composites," Journal of Polymer Science, Polymer Chemistry, 2012, 50,4369-4402. Wiley Online Library.
Peutzfeldt, A., "Resin Composites in Dentistry: The Monomer Systems," European Journal of Oral Sciences, 1997, 97-116. Munksgaard.

* cited by examiner

*Primary Examiner* — Mohammad M Ameen
(74) *Attorney, Agent, or Firm* — Ann M. Knab; Thad McMurray

(57) ABSTRACT

Radically polymerizable dental material, which contains at least one ABA or AB block copolymer, preferably at least one monofunctional, radically polymerizable monomer (a) and preferably at least one radically polymerizable urethane di(meth)acrylate telechel (b).

12 Claims, No Drawings

TRANSPARENT, FRACTURE-TOUGH POLYMERIZATION RESINS FOR THE PRODUCTION OF DENTAL SHAPED BODIES

CROSS-REFERENCE TO RELATED APPLICATIONS

This application claims priority to European Patent Application No. 21172707.8 filed on May 7, 2021, the disclosure of which is incorporated herein by reference in its entirety.

TECHNICAL FIELD

The present invention relates to radically polymerizable compositions, which are particularly suitable as dental material for the production of dental shaped bodies, such as artificial teeth, dental prostheses, inlays, onlays, splints (bite splints), crowns, bridges, veneering materials and orthodontic appliances, by additive processes.

BACKGROUND

Conventional dental polymerization systems mostly consist of a mixture of transparent liquid monomers, initiator components, stabilizers and pigments (J. Viohl, K. Dermann, D. Quast, S. Venz, Die Chemie zahnärztlicher Füngskunststoffe, Carl Hanser Verlag, Munich-Vienna 1986, 21-27). Mixtures of dimethacrylates are mostly used as monomers for building polymer networks, e.g. in filling materials (cf. A. Peutzfeldt, Resin composites in dentistry: The monomer systems, Eur. J. Oral. Sci. 105 (1997) 97-116; N. Moszner, T. Hirt, New Polymer-Chemical Developments in Clinical Dental Polymer Materials: Enamel-Dentin Adhesives and Restorative Composites, J. Polym. Sci. Part A: Polym. Chem. 50 (2012) 4369-4402). Examples of these are the high-viscosity dimethacrylates 2,2-bis[4-(2-hydroxy-3-methacryloyloxypropyl)phenyl]propane (bis-GMA) and 1,6-bis-[2-methacryloyloxyethoxycarbonylamino]-2,4,4-trimethylhexane (UDMA) and the low-viscosity dimethacrylates bismethacryloyloxymethyltricyclo[5.2.1.]decane (TCDMA), decanediol-1,10-dimethacrylate ($D_3MA$) and triethylene glycol dimethacrylate (TEGDMA), used as diluting monomers. In contrast, the monofunctional monomer methyl methacrylate (MMA) is predominantly used for dental prostheses, which although it is low-viscosity is very volatile.

Depending on the field of use, further additives and initiators suitable for initiating the radical polymerization are added. Photoinitiators for the visible range, which form radicals with blue light and are characterized by a good curing depth and very good whitening properties, are used for initiating polymerization using light. Prosthetic materials contain powdered polymethyl methacrylate (PMMA), which forms a paste with MMA, as an essential component. The curing is effected thermally or with redox initiators. In the case of filling composites and luting cements, high proportions of inorganic fillers provide for a high flexural strength and surface hardness, wherein, however, fillers can have a disadvantageous effect on the transparency.

A major problem of radical methacrylate polymers is polymerization shrinkage ($\Delta V_P$), i.e. the contraction in volume of the methacrylate monomers used that occurs during the polymerization, which can lead e.g. to a very disadvantageous formation of marginal gaps in the case of filling composites and negatively influences the dimensional stability ($\Delta V_P$ is e.g. 21.0 vol.-% in the case of pure MMA) in the case of prosthetic materials.

A further disadvantage of PMMA or dimethacrylate polymers is the high level of brittleness of the materials. Low fracture toughness is an inherent property of the amorphous PMMA glass and, in the case of the polymer networks formed by dimethacrylate mixtures, is above all caused by their very irregular network structure.

In recent years, additive manufacturing processes have attracted increasing interest and found widespread use for the production of dental shaped bodies. In additive manufacturing processes, which are also referred to as generative manufacturing processes, 3D shaped bodies are generated in layers from polymerizable materials starting from a CAD dataset, wherein the layers are cured by controlled exposure to light. In stereolithography (SL), a UV laser is used as light source. In the DLP process (Digital Light Processing), a projectable image is used for the curing of the photopolymerization resin in layers.

Building materials for the additive production of dental shaped bodies must meet various requirements in view of the characteristic features of this process. They should have a low viscosity and a high transparency and good mechanical properties after curing. The materials disclosed in the state of the art are optimized with respect to particular properties, often at the expense of other properties.

The use of mono- and polyfunctional methacrylates as resins for additive processes is the subject of numerous patents and patent applications.

U.S. Pat. No. 10,562,995 B2, which is hereby incorporated by reference, discloses polymerization resins for the stereolithographic production of dental prostheses which are based on mixtures of aromatic di(meth)acrylates, which have no OH or COOH groups, with (meth)acrylic monomers, which contain at least one OH or COOH group.

U.S. Pat. No. 10,568,814 B2, which is hereby incorporated by reference, discloses photopolymerizable compositions for the production of artificial teeth and denture bases by 3D printing, which are said to have a high flexural strength and a high modulus of elasticity after curing. The materials are based on a mixture of ethoxylated bisphenol A dimethacrylate, monofunctional methacrylates and urethane dimethacrylates.

EP 3 020 361 A1 and corresponding U.S. Pat. No. 9,795,541B2, which is hereby incorporated by reference, relate to curable compositions for additive manufacturing processes, which contain radically polymerizable polysiloxanes and disiloxanes. The materials are said to be characterized by a high dimensional stability and improved biocompatibility.

EP 3 494 954 A1 and corresponding U.S. Ser. No. 10/973,742B2, which is hereby incorporated by reference, disclose photopolymerizable compositions for the production of dental prostheses which contain a mixture of aromatic acrylates with a molar mass of from 200 to 800 g/mol and at least one further (meth)acrylate, which can contain aromatic and non-aromatic rings. The materials are said to be characterized by a good Charpy fracture toughness.

EP 3 564 206 A1 discloses (meth)acryloxy-substituted benzoic acid esters, which are said to be suitable as reactive diluents for additive manufacturing processes.

Dental shaped bodies must have a good fracture toughness and at the same time a good flexural strength and a high modulus of elasticity. An improvement in the fracture toughness can be achieved by internal plasticization, e.g. through the addition of flexible monomers. These have the disadvantage that they significantly reduce the flexural strength and the modulus of elasticity of the polymers. According to the state of the art, polymer particles with a core-shell structure, which result in a relatively good flexural strength and a relatively high modulus of elasticity, are therefore usually added to the polymerization resins as so-called impact modifiers to improve the fracture toughness.

WO 2014/078537 A1 and corresponding US2014131908A1, which is hereby incorporated by reference, disclose resin mixtures for the production of dental shaped bodies by 3D printing processes based on mono- and multifunctional methacrylates, which contain silicone acrylate-based impact modifiers with a core-shell structure for improving the impact resistance and fracture toughness.

US 2018/0000570 A1, which is hereby incorporated by reference, relates to building materials based on mono- and multifunctional (meth)acrylates for the additive production of dental components. The building materials contain rubber particles based on silicone acrylic with a core-shell structure (product S2006 from Mitsubishi Rayon Co.) as impact modifiers and oligomers, which are prepared by reacting trimethyl 1,6-diisocyanate, bisphenol A propoxylate and 2-hydroxyethyl methacrylate (HEMA). The cured components are said to have good mechanical and physical properties as well as a good biocompatibility.

U.S. Pat. No. 10,299,896 B2 and US 2019/0053883 A1, which are hereby incorporated by reference, disclose dental components produced by additive processes which have at least two layers of building materials with different compositions. One layer is formed by a material which contains oligomers, which are obtained by reacting intermediate products having terminal isocyanate groups with hydroxyl-based methacrylates, a polymerizable acrylic compound and an impact modifier. At least one further layer is formed by a material which contains a urethane monomer, a glycol dimethacrylate and filler. The combination of materials with different mechanical and physical properties is said to be advantageous for adapting the components to different requirements. Commercially available polymers with a core-shell structure, such as e.g. the product M570 from Kaneka, are used as impact modifiers.

EP 3 564 282 A1 discloses curable compositions for high-temperature photopolymerization processes which contain an oligomeric urethane dimethacrylate as glass transition temperature modifier, a (poly)carbonate-(poly) urethane dimethacrylate as toughness modifier and optionally core-shell particles. They are said to have good thermomechanical properties and good biocompatibility and to be suitable for the production of orthodontic appliances.

The mode of action of impact modifiers with a core-shell structure is based on an interaction between the tip of a forming crack and the core-shell polymer particles. These particles have a relatively soft polymer core and a hard polymer shell. If a crack tip meets such a particle, a cavity is formed in the core and the polymer shell is separated off from the polymerized resin matrix as well as the core being separated off from the shell, and thus a space is formed (cavitation) for plastic deformation surfaces. A major disadvantage for dental applications is that core-shell polymers (CSP) significantly reduce the transparency of the materials, which has a disadvantageous effect on the stereolithographic construction process.

SUMMARY

The object of the invention is to provide materials for the production of dental shaped bodies which have a property profile optimized for additive processes. In particular, the materials should have a high transparency in combination with a good fracture toughness and high fracture work. Moreover, they should exhibit a low viscosity and good mechanical properties after storage in water as well as a good biocompatibility.

DETAILED DESCRIPTION

According to the invention, this object is achieved by radically polymerizable dental materials, which contain at least one ABA or AB block copolymer. Moreover, the dental materials preferably contain at least one monofunctional, radically polymerizable monomer (a) and preferably also at least one radically polymerizable urethane di(meth)acrylate telechel (b).

The dental materials according to the invention preferably have the following composition:

(a) 30 to 70 wt.-%, preferably 30 to 61 wt.-% and particularly preferably 40 to 60 wt.-% of at least one aromatic, bicyclic or tricyclic mono(meth)acrylate, (b) 20 to 60 wt.-%, preferably 30 to 55 wt.-% and particularly preferably 33 to 55 wt.-% of at least one urethane di(meth)acrylate telechel with a number-average molar mass of from 750 to 2000 g/mol, (c) 0 to 30 wt.-%, preferably 0 to 20 wt.-% and particularly preferably 0 wt.-% di(meth)acrylate monomer(s), (d) 1 to 12 wt.-%, preferably 2 to 12 wt.-% and particularly preferably 2 to 10 wt.-% of at least one ABA and/or AB block copolymer, wherein the A block or blocks are homogeneously miscible with the mixture of components (a) to (c) and the B block is not homogeneously miscible with the mixture of components (a) to (c), and (e) 0.1 to 5.0 wt.-%, preferably 0.2 to 4.0 wt.-% and particularly preferably 0.3 to 3.0 wt.-% of at least one initiator for the radical polymerization.

Unless otherwise stated, all percentages by weight herein relate to the total mass of the material.

The dental materials according to the invention preferably contain as component (a) at least one aromatic, bicyclic or tricyclic mono(meth)acrylate of Formula (I)

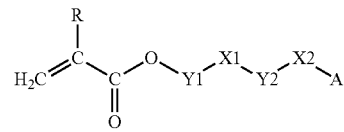

Formula I in which the variables have the following meanings:

A is an aromatic group with 6 to 15 carbon atoms or a bicyclic or tricyclic aliphatic group with 7 to 10 carbon atoms, wherein A can be unsubstituted or substituted by one or more $C_1$-$C_5$ alkyl groups, $C_1$-$C_5$ alkoxy groups and/or chlorine atoms;

R hydrogen or methyl;

$X^1$, $X^2$ independently of each other are in each case absent or an ether, ester or urethane group, wherein $X^1$ is absent if $Y^1$ is absent and wherein $X^2$ is absent if $Y^2$ is absent;

$Y^1$, $Y^2$ independently of each other are in each case absent or a branched or preferably linear aliphatic hydrocarbon radical with 1 to 10 carbon atoms, which can be interrupted by 1 to 3 oxygen atoms.

Herein, (meth)acrylate represents acrylate, methacrylate or a mixture thereof, wherein in all cases the meaning methacrylate is preferred.

All formulae shown herein extend only to those compounds which are compatible with the theory of chemical valence. The indication that a radical is interrupted e.g. by one or more oxygen atoms is to be understood to mean that these atoms are inserted in each case into the carbon chain of the radical. These atoms are thus bordered on both sides by C atoms and cannot be terminal. $C_1$ radicals cannot be branched or interrupted. Corresponding to the usual nomenclature, by aromatic hydrocarbon radicals is also meant those radicals which contain aromatic and non-aromatic groups. A preferred aromatic radical is, for example, 2,2-diphenylpropane.

The preferred, particularly preferred and quite particularly preferred definitions given for the individual variables can be selected in each case independently of each other. Compounds in which all the variables have the preferred, particularly preferred and quite particularly preferred definitions are naturally particularly suitable according to the invention.

Preferred aromatic groups A are benzene, biphenyl and 2,2-diphenylpropane:

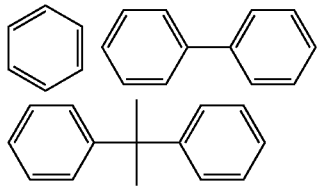

Preferred bicyclic aliphatic groups A are bicyclo[4.4.0]decane, bicyclo[4.3.0]nonane, bicyclo[2.2.2]octane and bicyclo[2.2.1]heptane:

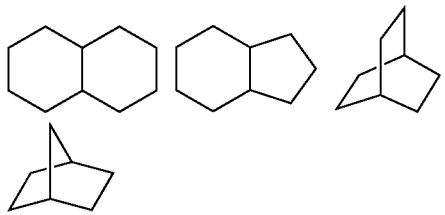

A preferred tricyclic aliphatic group A is tricyclo[5.2.1.0$^{2,6}$]decane:

Preferred aromatic mono(meth)acrylates (a) are 2-phenoxyethyl (meth)acrylate, 2-(o-biphenyloxy)ethyl (meth)acrylate, 2-hydroxy-3-phenoxypropyl (meth)acrylate, 2-[(benzyloxycarbonyl)-amino]-ethyl (meth)acrylate, 2-[(benzylcarbamoyl)-oxy]-ethyl (meth)acrylate, 1-phenoxypropan-2-yl (meth)acrylate and 2-(p-cumylphenoxy)-ethyl (meth)acrylate. Particularly suitable aromatic mono (meth)acrylates are 2-phenoxyethyl (meth)acrylate, 2-(o-biphenyloxy)ethyl (meth)acrylate, 2-hydroxy-3-phenoxypropyl (meth)acrylate, 2-[(benzyloxycarbonyl)amino]-ethyl (meth)acrylate, 1-phenoxypropan-2-yl (meth)acrylate, 2-(benzyloxy)ethyl (meth)acrylate, 3-phenoxybenzyl (meth)acrylate, phenoxypropyl (meth)acrylate, 2-benzyloxyethyl (meth)acrylate, 2-benzoyloxyethyl (meth)acrylate, 2-(meth)acryloyloxybenzoic acid methyl ester, 2-phenylethyl (meth)acrylate and/or 2-(p-cumylphenoxy)ethyl (meth)acrylate.

Preferred bi- or tricyclic mono(meth)acrylates (a) are tricyclodecane (meth)acrylate, tricyclodecane methyl (meth)acrylate and in particular 4,7,7-trimethylbicyclo[2.2.1]heptanyl (meth)acrylate.

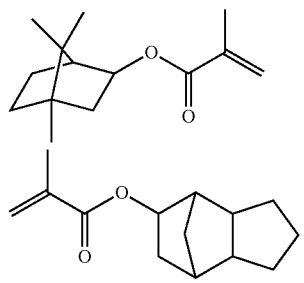

The aromatic, bicyclic or tricyclic monomethacrylates of Formula (I) used according to the invention are characterized by a good radical polymerizability. In addition, the polymers of these monomethacrylates have a comparatively low polymerization shrinkage and good mechanical properties. Because of their relatively high molar mass (150 to 350 g/mol) and their relatively non-polar structure, the mono (meth)acrylates of Formula (I) also have a low volatility and a comparatively low viscosity.

The dental materials according to the invention contain as component (b) at least one urethane dimethacrylate telechel with a molar mass of from 750 to 2000 g/mol. Component (b) contains two radically polymerizable groups and thus acts as crosslinker during the polymerization of the materials according to the invention, that is to say it leads to the formation of polymer networks. Because of the relatively high molar mass of component (b), polymers with a low network density and low polymerization shrinkage are obtained.

Unless otherwise stated, the molar mass of oligomers and polymers herein is the number-average molar mass, the absolute values of which can be determined using the known methods of freezing point depression (cryoscopy), boiling point elevation (ebullioscopy) or from the decrease in the vapour pressure (vapour pressure osmometry). The number-average molar mass of oligomers and polymers is preferably determined by means of gel permeation chromatography (GPC). This is a relative method in which the molecules are separated on the basis of their size, more specifically on the basis of their hydrodynamic volume. The absolute molar mass is determined through calibration with known standards.

Urethane dimethacrylate telechels (b) are preferably obtained by reacting diisocyanates with diols (HO-DA-OH) and then reacting the α,ω-isocyanate-functionalized urethane telechels with HEMA or HPMA. DA preferably represents an aromatic or aliphatic hydrocarbon radical with 6 to 33 carbon atoms, preferably a divalent polycyclic hydrocarbon radical, in particular an o-diphenyl, p-diphenyl or bisphenol A radical, or a branched or preferably linear $C_2$-$C_{18}$ alkylene group. The hydrocarbon radicals can contain one or more O atoms and/or S atoms, wherein O atoms are preferred.

Preferred diols of the formula HO-DA-OH are ethoxylated or propoxylated bisphenol A, o-diphenyl or p-diphenyl with 2 to 6 ethoxy or propoxy groups as well as $C_2$-$C_{18}$ alkanediols, which can contain 1 to 4 O or S atoms in the carbon chain. Particularly preferred diols are ethoxylated or propoxylated bisphenol A with 2, 3 or 4 ethoxy or propoxy groups, hexane-1,6-diol, octane-1,8-diol, nonane-1,9-diol, decane-1,10-diol or dodecane-1,12-diol, tetra- or pentaethylene glycol. Ethoxylated or propoxylated bisphenol A with 2 or 3 ethoxy or propoxy groups, decanediol, undecanediol or dodecanediol as well as cyclic or polycyclic aliphatic diols, in particular cyclohexanediol, norbornanediol, tricyclodecanediol and tricyclodecanedimethanol (octahydro-4,7-methano-1H-indenedimethanol), are quite particularly preferred.

Preferred diisocyanates are hexamethylene-1,6-diisocyanate (HMDI), 2,2,4-trimethylhexamethylene-1,6-diisocyanate (TMDI), 1-isocyanato-3-isocyanatomethyl-3,5,5-trimethylcyclohexane (isophorone diisocyanate, IPDI), m-tetramethylxylylene diisocyanate (1,3-bis(2-isocyanato-2-propyl)benzene, TMXDI), toluene-2,4-diisocyanate (TDI), diphenylmethane-4,4'-diisocyanate (MDI) and 1-isocyanato-4-[(4-isocyanatocyclohexyl)methyl]cyclohexane ($H_{12}$MDI), wherein IPDI is particularly preferred.

Telechels in accordance with general formula (II) are preferred according to the invention

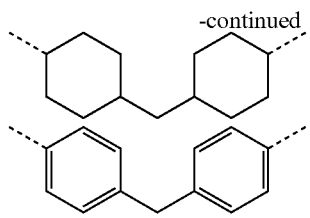

preferably:

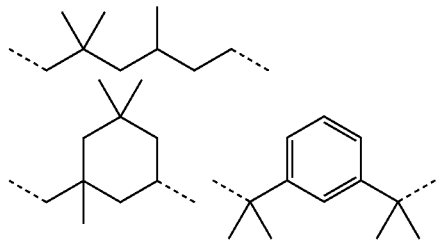

DA a structural element, which is derived from the diols HO-DA-OH by cleaving the hydrogen atoms from the two hydroxyl groups.

The urethane dimethacrylate telechels preferred according to the invention are characterized by a good radical polymerizability. Moreover, they give the cured materials good cohesive properties.

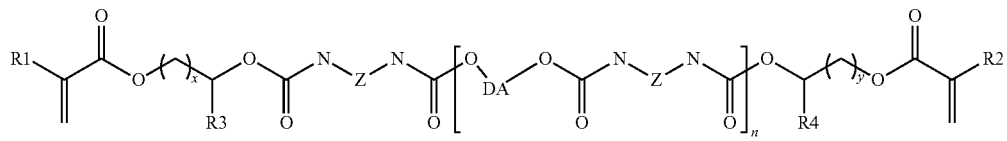

Formula II in which the variables have the following meanings:
- $R^1$, $R^2$ independently of each other in each case H or methyl, preferably methyl,
- $R^3$, $R^4$ independently of each other in each case H or methyl, preferably methyl,
- x, y independently of each other in each case an integer from 1 to 11, preferably 1 to 5,
- n 1, 2 or 3, preferably 1
- Z

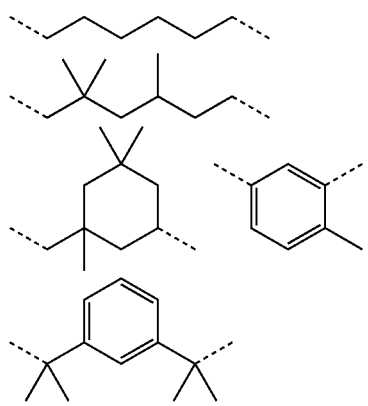

Monofunctional methacrylates (a), urethane dimethacrylate telechels (b) and optionally further radically polymerizable monomers are preferably used in a proportion such that crosslinked polymers with a network density of below $v_c$=300 to 5000 mol/m$^3$, particularly preferably 400 to 3000 mol/m$^3$ are obtained. The crosslinking density is substantially determined by the ratio of crosslinking monomers to monofunctional monomers. Dental materials in which the mole fraction of the crosslinking monomers lies in a range of from 0.1 to 0.6 and particularly preferably 0.15 to 0.45 are preferred according to the invention. All radically polymerizable components of the materials according to the invention are used to calculate the mole fraction, that is in particular components (a) to (c) and optionally further radically polymerizable monomers. By crosslinking monomers is meant all radically polymerizable components which have two or more radically polymerizable groups, that is in particular components (b) and (c). Crosslinking monomers are also referred to as polyfunctional monomers. Monofunctional monomers are monomers with only one radically polymerizable group.

The network density corresponds to the number of nodes (in mol) per unit of volume and can be calculated from the plateau value of the storage modulus G' in the elastic region through dynamic mechanical measurements. The glass transition temperature $T_g$ and the network density $v_c$ are determined using a rheometer, preferably an Anton Paar MCR301 rheometer. For this, the storage and loss modulus of a test piece (25×5×1 mm, clamped lengthways) are measured between 25° C. and 250° C. (frequency 1 Hz, deformation 0.05%, heating rate 2 K/min). $T_g$ is the maximum of the loss factor tan δ (ratio of loss modulus to storage modulus). The network density is calculated according to the formula $v_c=G'/(RT)$, where G' is the storage modulus at the temperature $T_g+50$ K, R is the generic gas constant and T is the temperature at $T_g+50$ K in Kelvin.

To further set the crosslinking density and to influence the mechanical properties of the polymers, the dental materials according to the invention can additionally contain further di(meth)acrylate monomers (c) in addition to components (a) and (b).

Preferred di(meth)acrylates (c) are bisphenol A dimethacrylate (bis-GMA, an addition product of methacrylic acid and bisphenol A diglycidyl ether), ethoxylated or propoxylated bisphenol A dimethacrylate, such as e.g. the bisphenol A dimethacrylate SR-348c (Sartomer) with 3 ethoxy groups, 2,2-bis[4-(2-methacryloxypropoxy)phenyl]propane (UDMA, an addition product of HEMA and TMDI), V380 (an addition product of a mixture of 0.7 mol 2-hydroxyethyl methacrylate and 0.3 mol 2-hydroxypropyl methacrylate with 1 mol α,α,α',α'-tetramethyl-m-xylylene diisocyanate), bis(methacryloyloxymethyl)tricyclo-[$5.2.1.0^{2,6}$]decane (DCP), di-, tri- or tetraethylene glycol dimethacrylate, trimethylolpropane trimethacrylate, pentaerythritol tetra(meth)acrylate, as well as glycerol di- and glycerol trimethacrylate, 1,4-butanediol dimethacrylate, 1,10-decanediol dimethacrylate ($D_3MA$) and 1,12-dodecanediol dimethacrylate.

The di(meth)acrylate monomers (c) are characterized by a relatively low molar weight. Di(meth)acrylates (c) with a molar weight in the range of from 200 to 800 g/mol, preferably 220 to 650 g/mol, are preferred according to the invention. Due to the low molar weight in comparison with the urethane di(meth)acrylate telechels (b), the di(meth)acrylate monomers (c) bring about a relatively strong crosslinking of the polymers and thus result in a high network density, which can have a disadvantageous effect on the fracture toughness. The proportion of further di(meth)acrylates is therefore limited to a maximum of 30 wt.-%, preferably a maximum of 10 wt.-%. According to a particularly preferred embodiment, the dental materials according to the invention contain exclusively the urethane di(meth)acrylate telechels (b) as crosslinker.

Moreover, the dental materials according to the invention can contain further mono(meth)acrylates in addition to component (a). The proportion of further mono(meth)acrylates preferably lies below 10 wt.-%, wherein materials which contain no further mono(meth)acrylates are particularly preferred.

The dental materials according to the invention contain as component (d) at least one ABA and/or one AB block copolymer. By block copolymers is meant macromolecules which consist of two or more homopolymer blocks covalently bonded to each other.

Block copolymers preferred according to the invention can be prepared using the known methods of living or controlled polymerization, for example by radical or ionic (anionic and cationic) polymerization, wherein controlled radical polymerization and living anionic polymerization are preferred. However, block copolymers can also be obtained by coupling end groups of homopolymers. The block copolymers used according to the invention can be present as di- and triblock copolymers.

AB block copolymers can be prepared, for example, by coupling an A block with a terminal OH group by esterification with a B block, which has a COOH group. End-group-functionalized homopolymer blocks can be prepared relatively easily using the methods of controlled radical polymerization or by end-capping in the case of anionic polymerization.

For example, the monomer A is anionically polymerized and an OH group is inserted by end-capping. The OH end group can then be esterified e.g. with α-bromoisobutyric acid. The bromine end group obtained in the process then functions as start centre for the formation of the B block through ATRP (Atom Transfer Radical Polymerization) of monomer B, initiated by metal complexes, for example of Cu(I), Ru(I) or Fe(II).

Triblock copolymers can be prepared analogously. For example, a B block is prepared through anionic polymerization of monomer B via a dianion mechanism. The B mid-block formed carries an anion end group on each side, which initiates the anionic polymerization of monomer A, forming the two A blocks (method 1). The esterification of a telechelic B block, which carries a suitable functional group, e.g. an OH group, on both ends in each case, with two A blocks, which are functionalized on only one side, e.g. with a COOH group, gives ABA triblock copolymers (method 2). Finally, OH-telechelic homopolymers of monomer B can be esterified with α-bromoisobutyric acid. The two thus-formed bromine end groups in the homopolymer block B can then be utilized as start centre for the formation of the two A blocks through ATRP (method 3).

Terminal or pendant polymerizable methacrylate groups can also be inserted during the synthesis of the block copolymers. These bring about a better integration of the block copolymers into the polymer networks formed through radical copolymerization of the methacrylate groups.

The monomers are preferably chosen such that the A blocks are miscible with the resin matrix, i.e. the mixture of constituents (a) to (c), and the B block is not miscible with the resin matrix.

Here, the miscibility is meant in the sense of thermodynamics in relation to the single-phase state. According to this, by a miscible polymer block is meant a polymer block consisting of a monomer, the homopolymer of which is soluble in the resin matrix, with the result that the mixture has a transparency of at least 95%. In contrast, if the mixture is cloudy or opaque, i.e. the transparency is lower than 95%, then the homopolymer, and thus the corresponding polymer block, is not miscible with the resin matrix. The transparency is measured in transmission (D65) in accordance with the ISO 10526:1999 standard on 1 mm-thick test pieces polished to high gloss using a spectrophotometer, e.g. using a Konika-Minolta CM-S-type spectrophotometer.

The block copolymers bring about a significant improvement in the fracture toughness of the materials according to the invention after curing. It is assumed that the immiscibility of the B blocks of the block copolymers with the remaining constituents of the compositions according to the invention brings about a microphase separation and thus the formation of morphologies at the nanoscale level. Here, the macromolecules of the ABA or AB block copolymers form spherical or worm-like phases in the monomer resin or, during the curing, by self-assembly, which phases can interact with crack tips, that is to say crack tips meet the phases and the fracture energy is distributed into the phases such that the cracks do not migrate further through the material and do not increase in size. The growth of a crack can be observed under an electron microscope in transparent materials. In fracture mechanics, the frontmost part of the crack is called the crack tip.

Block copolymers preferred according to the invention are AB diblock and ABA triblock copolymers.

The A block is a polymer, preferably an oligomer, which is made up of one or more of the following monomers: cyclic, aliphatic esters or ethers, arylene oxide, alkylene oxide, radically polymerizable monomers, for example α,β-unsaturated acids and α,β-unsaturated acid esters. The A block is preferably a poly(meth)acrylate oligomer, polylactone oligomer, phenylene oxide oligomer or polyalkylene oxide oligomer. Quite particularly preferably, the A block is a polymer of caprolactone, 2,6-dialkyl-1,4-phenylene oxide and in particular of 2,6-dimethyl-1,4-phenylene oxide, ethylene oxide, propylene oxide or (meth)acrylates. The A block is thus preferably a polycaprolactone (PCL) oligomer, poly(2,6-dimethyl-1,4-phenylene oxide) oligomer, poly(ethylene oxide) oligomer, poly(propylene oxide) oligomer or poly(meth)acrylate oligomer.

The B block is preferably a polysiloxane oligomer and/or a polyvinyl oligomer and/or a polyalkene oligomer and/or a polydiene oligomer. Particularly preferably, the B block is a polydiene oligomer, polyvinyl alkanoate oligomer or a polysiloxane oligomer in accordance with the formula —O—(SiR$^5_2$—O)$_p$—, in which R$^5$ is a linear $C_1$-$C_{20}$ alkyl, branched $C_3$-$C_{12}$ alkyl or $C_6$-$C_{20}$ aryl group, wherein the individual R$^5$ radicals can be identical or different, and p is a number from 3 to 100, preferably a number from 10 to 50.

Quite particularly preferably, the B block is a polymer of dimethylchlorosilane, cyclotri- or cyclotetradimethoxysilane, isoprene, vinyl acetate, isobutene, cis-butadiene or ethylene. The B block is thus preferably a poly(dimethylsiloxane) (PDMS) oligomer, poly(isoprene) oligomer, poly(vinyl acetate) oligomer, poly(isobutene) oligomer, cis-poly(butadiene) oligomer or poly(ethylene) oligomer.

The B blocks are characterized by a relatively high flexibility. By flexible blocks is meant blocks which are formed from monomers, the homopolymers of which have a glass transition temperature $T_G$ below 50° C., preferably below 0° C. and quite particularly preferably in the range of from −30 to −110° C. Block copolymers with flexible blocks improve the fracture toughness, but impair the flexural strength and the modulus of elasticity of the polymers much less than internal plasticizers.

Polyester-polysiloxane block copolymers in accordance with the following general formula are preferred according to the invention:

(PCL)$_q$-b-(PDMS)$_r$-b-(PCL)$_q$ in which q in each case is a number from 5 to 40, preferably 10 to 20, and r is a number from 10 to 100, preferably 30 to 60.

(PCL)$_q$ represents polycaprolactone, which is made up of q caprolactone monomers, and (PDMS)$_r$ for poly(dimethylsiloxane), which is made up of r dimethylsiloxane monomers. The letter b represents block.

Poly(meth)acrylate-polysiloxane block copolymers which contain a polymethyl methacrylate radical as A block and a polysiloxane radical as B block, wherein the polysiloxane radical is preferably as defined above and is quite particularly preferably a poly(dimethylsiloxane) radical, are further preferred.

Particularly preferably, the ABA triblock copolymers are PCL-b-PDMS-b-PCL and PMMA-b-PDMS-b-PMMA with a molar ratio A:B of from 0.1 to 5 and with a molar mass preferably of from 3 to 25 kDa, particularly preferably 4 to 20 kDa and quite particularly preferably 5 to 10 kDa. A preferred block copolymer is PCL-b-PDMS-b-PCL, wherein the PDMS blocks have a molar mass of approx. 3200 g/mol and the PCL blocks have a molar mass of in each case approx. 1600 g/mol. PCL represents polycaprolactone, PDMS poly(dimethylsiloxane) and PMMA polymethyl methacrylate.

The block copolymer or block copolymers are preferably used in a quantity of from 1 to 12 wt.-%, particularly preferably in a quantity of from 2 to 10 wt.-% and quite particularly preferably 3 to 8 wt.-%, relative to the total weight of the dental material.

It was found that the block copolymers used according to the invention significantly improve the fracture toughness of the polymer networks, without impairing the transparency. Moreover, they bring about only a relatively small increase in viscosity. A further advantage of the block copolymers used according to the invention is that they can easily be homogeneously mixed with the remaining components of the materials, whereas the homogeneous dispersion of core-shell polymer particles is much more complex. In addition, particles tend towards sedimentation, with the result that compositions based on core-shell particles are less stable. On the other hand, the block copolymers can be incorporated well into resin mixtures, with the result that it is possible to match the materials to the planned application and to set the desired fracture toughness and fracture work without problems.

The dental materials according to the invention contain as component (e) at least one initiator for the radical polymerization, preferably a photoinitiator.

Preferred photoinitiators are benzophenone, benzoin and their derivatives as well as α-diketones and their derivatives, such as 9,10-phenanthrenequinone, 1-phenyl-propane-1,2-dione, diacetyl or 4,4'-dichlorobenzil. Camphorquinone (CQ) and 2,2-dimethoxy-2-phenyl-acetophenone are particularly preferably used, and α-diketones in combination with amines as reducing agent, such as e.g. 4-(dimethylamino)benzoic acid ester (EDMAB), N,N-dimethylaminoethyl methacrylate, N,N-dimethyl-sym-xylidine or triethanolamine, are quite particularly preferably used. Preferred monomolecular photoinitiators for the visible range are monoacyltrialkyl-, diacyldialkyl- and tetraacylgermanium as well as tetraacylstannanes, such as e.g. benzoyltrimethylgermanium, dibenzoyldiethylgermanium, bis(4-methoxybenzoyl)-diethylgermanium, tetrakis(2-methylbenzoyl)germane or tetrakis(mesitoyl)stannane. Mixtures of the different photoinitiators can also be used, such as e.g. bis(4-methoxybenzoyl)diethylgermanium in combination with camphorquinone and 4-dimethylaminobenzoic acid ethyl ester.

Preferred initiators for curing the dental materials according to the invention with UV light are Norrish type I photoinitiators, above all acetophenones, e.g. 2,2-diethoxy-1-phenylethanone, benzoin ethers e.g. Irgacure 651 (benzil dimethyl ketal), hydroxyalkylphenylacetophenones, e.g. Irgacure 184 (1-hydroxycyclohexyl phenyl ketone), acyl- or bisacylphosphine oxides, e.g. Irgacure TPO (2,4,6-trimethylbenzoyldiphenylphosphine oxide) and Irgacure 819 (bis (2,4,6-trimethylbenzoyl)phenylphosphine oxide). Further preferred photoinitiators are 2-benzyl-2-(dimethylamino)-4'-morpholinobutyrophenone (Irgacure 369) and 1-butanone-2-(dimethylamino)-2-(4-methylphenyl)methyl-1-4-

(4-morpholinyl)phenyl (Irgacure 379). Particularly preferred photoinitiators are bis(4-methoxybenzoyl)diethylgermanium, Irgacure TPO and Irgacure 819 as well as camphorquinone/4-(dimethylamino)benzoic acid ester. For a post-tempering, it is advantageous to use two photoinitiators which differ in their absorption ranges, such as e.g. Irgacure TPO and camphorquinone/4-(dimethylamino)benzoic acid ester.

The dental materials according to the invention can alternatively or additionally also contain thermal initiators, e.g. azo compounds, such as 2,2'-azobis(isobutyronitrile) (AIBN) or azobis-(4-cyanovaleric acid), or peroxides, such as dibenzoyl peroxide, dilauroyl peroxide, tert-butyl peroctoate, tert-butyl perbenzoate or di-(tert-butyl) peroxide. Combinations with aromatic amines can also be used to accelerate the initiation by means of peroxides. Preferred redox systems are combinations of dibenzoyl peroxide with amines, such as N,N-dimethyl-p-toluidine, N,N-dihydroxyethyl-p-toluidine, p-dimethylaminobenzoic acid ethyl ester, or structurally related systems.

The initiator or initiators are preferably used in a total quantity of from 0.1 to 5.0 wt.-%, particularly preferably 0.2 to 4 wt.-% and quite particularly preferably 0.3 to 3.0 wt.-%, wherein these quantities include all initiator constituents, such as e.g. reducing agents.

To further improve the fracture toughness and impact resistance, the dental materials according to the invention can also contain a certain proportion of one or more core-shell polymers (component (f)). Core-shell polymers (CSP) with a soft polymer core, e.g. consisting of a crosslinked butyl acrylate, and a rather hard polymer shell, e.g. PMMA, are preferred. By soft or flexible polymers is meant polymers with a glass transition temperature $T_G$ below 50° C., preferably below 0° C. and quite particularly preferably in the range of from −30 to −110° C. PDMS, with a $T_G$ of approx. −110° C., is a preferred specific example. By hard polymers is meant polymers with a glass transition temperature above 50° C. and preferably above 80° C. PMMA, with a $T_G$ of 100° C., is a preferred specific example.

The fracture toughness-modifying action of the CSP particles in radical dimethacrylate polymer networks depends above all on the type of the CSP particles, the particle size, the crosslinking density and the weight ratio of core to shell, which preferably lies in a range of from 1:1 to 200:1. The crosslinking density is substantially determined by the proportion of crosslinking monomers in the particle core. This preferably lies in a range of from 1 to 10 wt.-%, relative to the mass of the core. Particles with a particle size of from 0.20 to 5.0 μm are preferred according to the invention.

CSP particles with a core made of soft plastics, such as polybutadiene, polyisoprene, polybutyl acrylate, MMA-butadiene-styrene copolymers (MBS) or polydimethylsiloxane, and a shell made of hard plastics, such as PMMA or MMA-styrene copolymer, are preferred according to the invention. CSP particles suitable according to the invention are commercially available, e.g. from Arkema (Clearstrength), Soken (Chemisnow) or Kaneka (e.g. M521 or M210).

Core-shell polymers can be added in a quantity of up to 15 wt.-%. A disadvantage of the use of core-shell polymers is that they can greatly impair the transparency of the compositions, which has a negative effect on the curing depth in the case of photopolymerization and additionally has a negative aesthetic effect in the case of dental shaped bodies. Materials which contain at most 5 wt.-% and particularly preferably no core-shell particles are therefore preferred according to the invention. When incorporating the CSP particles into the dental material, a good dispersion is to be ensured.

To influence the mechanical properties, the dental materials according to the invention can be strengthened with inorganic particulate fillers (g).

Preferred inorganic fillers are oxides, such as $SiO_2$, $ZrO_2$ and $TiO_2$ or mixed oxides of $SiO_2$, $ZrO_2$, ZnO and/or $TiO_2$, nanoparticulate or microfine fillers, such as fumed silica or precipitated silica, glass powders, such as quartz, glass ceramic, borosilicate or radiopaque glass powders, preferably barium or strontium aluminium silicate glasses, and radiopaque fillers, such as ytterbium trifluoride, tantalum(V) oxide, barium sulfate or mixed oxides of $SiO_2$ with ytterbium(III) oxide or tantalum(V) oxide. The dental materials according to the invention can furthermore contain fibrous fillers, nanofibres, whiskers or mixtures thereof. According to a preferred embodiment, the materials according to the invention do not contain fluoroaluminosilicate glasses, calcium aluminium silicate glasses or other fillers which react with organic acids in the sense of an acid-base reaction.

Preferably, the oxides have a particle size of from 0.010 to 15 μm, the nanoparticulate or microfine fillers have a particle size of from 10 to 300 nm, the glass powders have a particle size of from 0.01 to 15 μm, preferably of from 0.2 to 1.5 μm, and the radiopaque fillers have a particle size of from 0.2 to 5 μm.

Particularly preferred fillers are mixed oxides of $SiO_2$ and $ZrO_2$, with a particle size of from 10 to 300 nm, glass powders with a particle size of from 0.2 to 1.5 μm, in particular radiopaque glass powders of e.g. barium or strontium aluminium silicate glasses, and radiopaque fillers with a particle size of from 0.2 to 5 μm, in particular ytterbium trifluoride and/or mixed oxides of $SiO_2$ with ytterbium(III) oxide.

To improve the bond between the filler particles and the crosslinked polymerization matrix, $SiO_2$-based fillers can be surface-modified with methacrylate-functionalized silanes. A preferred example of such silanes is 3-methacryloyloxypropyl-trimethoxysilane. For the surface modification of non-silicate fillers such as $ZrO_2$ or $TiO_2$, functionalized acidic phosphates, such as e.g. 10-methacryloyloxydecyl dihydrogen phosphate can also be used.

Further preferred fillers are particulate waxes, in particular carnauba wax, preferably with a particle size of from 1 to 10 μm, non-crosslinked or partially crosslinked polymethyl methacrylate (PMMA) particles, preferably with a particle size of from 500 nm to 10 μm, as well as polyamide-12 particles, preferably with a particle size of from 5 to 10 μm.

Moreover, the dental materials according to the invention can contain a so-called prepolymer filler or isofiller, i.e. a ground composite which preferably has a broad particle-size distribution, e.g. with particle sizes of from 0.05 to 20 μm, in particular approximately 0.1 to approximately 10 μm. The prepolymer filler or isofiller is preferably surface-modified, in particular silanized.

Unless otherwise stated, all particle sizes herein are weight-average particle sizes, wherein the particle-size determination in the range of from 0.1 μm to 1000 μm is effected by means of static light scattering, preferably using an LA-960 static laser scattering particle size analyzer (Horiba, Japan). Here, a laser diode with a wavelength of 655 nm and an LED with a wavelength of 405 nm are used as light sources. The use of two light sources with different wavelengths makes it possible to measure the entire particle-size distribution of a sample in only one measurement pass, wherein the measurement is carried out as a wet measurement. For this, a 0.1 to 0.5% aqueous dispersion of the filler is prepared and the scattered light thereof is measured in a flow cell. The scattered-light analysis for calculating particle size and particle-size distribution is effected in accordance with the Mie theory according to DIN/ISO 13320.

Particle sizes smaller than 0.1 µm are preferably determined by means of dynamic light scattering (DLS). The measurement of the particle size in the range of from 5 nm to 0.1 µm is preferably effected by dynamic light scattering (DLS) of aqueous particle dispersions, preferably using a Malvern Zetasizer Nano ZS (Malvern Instruments, Malvern UK) with an He—Ne laser with a wavelength of 633 nm, at a scattering angle of 90° at 25° C.

The light scattering decreases as the particle size decreases. Particle sizes smaller than 0.1 µm can also be determined by means of SEM or TEM spectroscopy. The transmission electron microscopy (TEM) is preferably carried out using a Philips CM30 TEM at an accelerating voltage of 300 kV. For the preparation of the samples, drops of the particle dispersion are applied to a 50 Å thick copper grid (mesh size 300), which is coated with carbon, and then the solvent is evaporated.

The fillers are divided according to their particle size into macrofillers and microfillers, wherein fillers with an average particle size of from 0.2 to 10 µm are called macrofillers and fillers with an average particle size of from approx. 5 to 100 nm are called microfillers. Macrofillers are obtained e.g. by grinding e.g. quartz, radiopaque glasses, borosilicates or ceramic and usually consist of splintery parts. Fumed $SiO_2$ or precipitated silica, or mixed oxides, e.g. $SiO_2$—$ZrO_2$, which are available by hydrolytic co-condensation of metal alkoxides, are preferably used as microfillers. The microfillers preferably have an average particle size of from approx. 5 to 100 nm. Fillers with a small particle size have a greater thickening action.

In a preferred embodiment, the dental materials according to the invention contain a mixture of two or more fillers, in particular of two or more fillers with different particle sizes. It was found that the use of such filler mixtures does not increase the viscosity of the materials excessively and the compositions can therefore be processed well using additive processes, such as e.g. using stereolithography. The total filler content preferably lies in a range of from 0 to 20 wt.-%, particularly preferably of from 0 to 10 wt.-%.

The dental materials according to the invention can furthermore contain one or more UV absorbers (h). The UV absorber serves to reduce the penetration depth of the light, and thus the polymerization depth, during the light-induced curing of the composition according to the invention. This proves to be advantageous in particular in the case of stereolithographic applications as only thin layers are to be cured in stereolithography. The use of a UV absorber can improve the precision in stereolithographic processes.

UV absorbers based on benzotriazole, benzophenone or triazines are preferred. Particularly preferred UV absorbers are 2,2'-methylenebis[6-(2H-benzotriazol-2-yl)-4-(1,1,3,3-tetramethylbutyl)phenol],2,2',4,4'-tetrahydroxybenzophenone, 2-tert-butyl-6-(5-chloro-2H-benzotriazol-2-yl)-4-methylphenol (bumetrizole), 2,2'-benzene-1,4-diylbis(4H-3,1-benzoxazin-4-one), 2-(4,6-bis-(2,4-dimethylphenyl)-1,3,5-triazin-2-yl)-5-(octyloxy)-phenol, 2-(2-hydroxy-5-methylphenyl)benzotriazole, 2-(2-hydroxyphenyl)benzotriazole, 2-(2H-benzotriazol-2-yl)-6-dodecyl-4-methylphenol, 2-(2'-hydroxy-3',5'-di-t-butylphenyl)-5-chlorobenzotriazole, 2,2'-dihydroxy-4-methoxybenzophenone and 2,2'-dihydroxy-4,4'-dimethoxybenzophenone. So-called Hindered Amine Light Stabilizers such as bis(1,2,2,6,6-pentamethyl-4-piperidyl) sebacate, methyl-1,2,2,6,6-pentamethyl-4-piperidyl sebacate, bis(1-octyloxy-2,2,6,6-tetramethyl-4-piperidyl) sebacate and bis(1,2,2,6,6-pentamethyl-4-piperidyl)-[[3,5-bis(1,1-dimethylethyl)-4-hydroxyphenyl]methyl]butyl malonate are further preferred. Quite particularly preferred UV absorbers are bumetrizole and 2,2',4,4'-tetrahydroxybenzophenone.

The UV absorber preferably has an absorption maximum which corresponds to the wavelength of the light used for the curing. UV absorbers with an absorption maximum in the range of from 320 to 500 nm and preferably 380 to 480 nm are advantageous, wherein UV absorbers with an absorption maximum below 400 nm are particularly preferred.

UV absorbers are optionally used in a quantity of from preferably 0 to 1.0 wt.-%, particularly preferably 0.01 to 0.5 wt.-%. Bumetrizole is preferably used in a quantity of from 0.01 to 0.2 wt.-%, particularly preferably 0.02 to 0.15 wt.-%, and 2,2',4,4'-tetrahydroxybenzophenone in a quantity of from 0.01 to 0.07 wt.-%. All data relate to the total weight of the material. Dental materials which do not contain a UV absorber are preferred.

The dental materials according to the invention can also contain one or more optical brighteners (i). Optical brighteners which absorb light in the UV range, i.e. light with a wavelength below 400 nm, are preferred according to the invention. Through the addition of an optical brightener, the penetration depth of the light, and thus the curing depth, can be reduced and the precision in stereolithographic processes can thus be increased. Optical brighteners which are capable of re-emitting light absorbed in the UV range as light with a wavelength of from 400 to 450 nm are particularly preferred. Such optical brighteners increase the reactivity of the materials because, due to their fluorescence, they emit the absorbed short-wave light as longer-wave blue light and thus provide additional luminous power for the photoinitiation. Optical brighteners preferred according to the invention are 2,5-bis(5-tert-butyl-benzoxazol-2-yl)thiophene and fluorescent agents in the form of terephthalic acid derivatives, such as e.g. 2,5-dihydroxyterephthalic acid diethyl ester or diethyl-2,5-dihydroxyterephthalate.

The optical brightener or optical brighteners are optionally used in a quantity of from preferably 0 to 0.1 wt.-%, particularly preferably 0.001 to 0.05 wt.-% and quite particularly preferably 0.002 to 0.02 wt.-%, in each case relative to the total weight of the material. Dental materials which do not contain an optical brightener are preferred.

Optical brighteners can be used in combination with UV absorbers. In this case, it is preferred that the weight ratio of UV absorber to optical brightener lies in a range of from 2:1 to 50:1, particularly preferably 2:1 to 30:1 and quite particularly preferably 2:1 to 5:1 or 10:1 to 25:1. Combinations which contain 2,2',4,4'-tetrahydroxybenzophenone or bumetrizole as UV absorber and 2,5-bis(5-tert-butyl-benzoxazol-2-yl)thiophene as optical brightener are preferred. The combination of 2,2',4,4'-tetrahydroxybenzophenone and 2,5-bis(5-tert-butyl-benzoxazol-2-yl)thiophene in a weight ratio of from 2:1 to 10:1, preferably 2:1 to 5:1, or the combination of bumetrizole and 2,5-bis(5-tert-butyl-benzoxazol-2-yl) thiophene in a weight ratio of from 5:1 to 30:1, preferably 10:1 to 20:1, is quite particularly preferred.

The dental materials according to the invention can additionally contain further additives (j), above all stabilizers, colorants, plasticizers, thixotropic additives, microbiocidal active ingredients and/or foaming agents.

The dental materials according to the invention preferably contain one or more stabilizers. These are free-radicalscavenging substances for preventing a premature polyreaction. The stabilizers are also called polymerization inhibitors. The inhibitors or stabilizers improve the storage stability of the materials.

Preferred inhibitors are phenols, such as hydroquinone monomethyl ether (MEHQ) or 2,6-di-tert-butyl-4-methylphenol (BHT). Phenols are preferably used in a concentration of from 0.001 to 0.50 wt.-%. Further preferred inhibitors are phenothiazine, the 2,2-diphenyl-1-picrylhydrazyl (DPPH) radical, the galvinoxyl radical, the triphenylmethyl radical and the 2,2,6,6-tetramethylpiperidine-1-oxyl (TEMPO) radical. These inhibitors are preferably used in a quantity of from 0.001 to 0.02 wt.-%. A polymerization does not take place until these additives have been used up. The quantities relate in each case to the total mass of the material. A mixture of inhibitors which contains at least one phenol and at least one of the further initiators is preferably used.

In addition, the dental materials according to the invention can also contain colorants, preferably in a concentration of from 0.0001 to 0.5 wt.-%. The colorants are primarily used for aesthetic purposes. Colorants preferred according to the invention are organic dyes and pigments, in particular azo dyes, carbonyl dyes, cyanine dyes, azomethines and methines, phthalocyanines and dioxazines. Dyes which are soluble in the materials according to the invention, in particular azo dyes, are particularly preferred. Moreover, inorganic and in particular organic pigments which can be dispersed well in the dental materials according to the invention are suitable as colorant. Preferred inorganic pigments are metal oxides or hydroxides, such as e.g. titanium dioxide or ZnO as white pigments, iron oxide ($Fe_2O_3$) as red pigment or iron hydroxide (FeOOH) as yellow pigment. Preferred organic pigments are azo pigments, such as e.g. monoazo yellow and orange pigments, diazo pigments or β-naphthol pigments, and non-azo or polycyclic pigments, such as e.g. phthalocyanine, quinacridone, perylene and flavanthrone pigments. Azo pigments and non-azo pigments are particularly preferred.

Moreover, the dental materials according to the invention can contain one or more plasticizers. Plasticizers prevent the polymers from becoming brittle after the photochemical curing and possible drying. In addition, plasticizers ensure sufficient flexibility. Plasticizers are preferably added in a concentration of from 0.2 to 5 wt.-%. Preferred plasticizers are phthalates, such as e.g. dibutyl or dihexyl phthalate, non-acidic phosphates, such as e.g. tributyl or tricresyl phosphate, n-octanol, glycerol or polyethylene glycols. Tartaric acid ester or citric acid ester, such as e.g. citric acid triester, which are characterized by a good biocompatibility, are particularly preferred.

The dental materials according to the invention can furthermore contain one or more thixotropic additives. These additives bring about a thickening of the materials and can thus, for example, prevent the fillers from sedimenting. In particular, filler-containing materials therefore preferably contain at least one thixotropic additive. Preferred thixotropic additives are OH group-containing polymers, such as e.g. cellulose derivatives, and inorganic substances, such as e.g. layer silicates. In order not to increase the viscosity of the materials too much, the dental materials according to the invention preferably contain only 0 to 3.0 wt.-%, particularly preferably 0 to 2.0 wt.-% and quite particularly preferably 0.1 to 2.0 wt.-% thixotropic additive, relative to the total weight of the material.

Certain fillers, such as e.g. highly dispersed $SiO_2$, i.e. $SiO_2$ with a small primary particle size (<20 nm) and a large surface area (>100 $m^2$), likewise have a thixotropic effect. Such fillers can replace thixotropic additives.

The rheological properties of the dental materials according to the invention are matched to the desired intended application. Materials for stereolithographic processing are preferably adjusted such that their viscosity lies in the range of from 50 mPa·s to 100 Pa·s, preferably 100 mPa·s to 10 Pa·s, particularly preferably 100 mPa·s to 5 Pa·s. The viscosity is determined at 25° C. using a cone-plate viscometer (shear rate 100/s). The dental materials according to the invention particularly preferably have a viscosity <10 Pa·s and quite particularly preferably <5 Pa·s at 25° C. The viscosity is preferably determined using an Anton Paar MCR 302-type viscometer with a CP25-2 cone-plate measuring system and a measuring gap of 53 μm in rotation at a shear rate of 100/s. Because of the low viscosity, the dental materials according to the invention are particularly suitable for being processed using additive manufacturing processes, such as e.g. 3D printing or stereolithography. The processing temperature preferably lies in a range of from 10 to 70° C., particularly preferably 20 to 30° C.

According to the invention, dental materials with the following composition are particularly preferred:
(a) 30 to 70 wt.-%, preferably 30 to 61 wt.-%, particularly preferably 40 to 60 wt.-% of at least one aromatic, bicyclic or tricyclic mono(meth)acrylate,
(b) 20 to 60 wt.-%, preferably 30 to 55 wt.-% and particularly preferably 33 to 55 wt.-% of at least one urethane di(meth)acrylate telechel with a number-average molar mass of from 750 to 2000 g/mol,
(c) 0 to 30 wt.-%, preferably 0 to 20 wt.-% and particularly preferably 0 wt.-% of di(meth)acrylate monomer(s),
(d) 1 to 12 wt.-%, preferably 2 to 12 wt.-%, particularly preferably 2 to 10 wt.-% of at least one ABA or AB block copolymer,
(e) 0.1 to 5.0 wt.-%, preferably 0.2 to 4.0 wt.-% and particularly preferably 0.3 to 3.0 wt.-% of at least one initiator for the radical polymerization,
(f) 0 to 15 wt.-%, preferably 0 to 5 wt.-% and particularly preferably 0 wt.-% of core-shell polymer particles,
(g) 0 to 20 wt.-%, preferably 0 to 15 wt.-% and particularly preferably 0 to 10 wt.-% of filler,
(h) 0 to 1.0 wt.-%, preferably 0 to 0.7 wt.-% and particularly preferably 0 to 0.5 wt.-% of UV absorber,
(i) 0 to 0.5 wt.-%, preferably 0 to 0.1 wt.-% and particularly preferably 0 to 0.05 wt.-% of optical brightener and
(j) 0 to 15 wt.-%, preferably 0 to 10 wt.-% and particularly preferably 0.05 to 5 wt.-% of further additives.

Dental materials with the following composition are quite particularly preferred:
(a) 30 to 70 wt.-%, preferably 30 to 61 wt.-% and particularly preferably 40 to 60 wt.-% of at least one mono(meth)acrylate of Formula (I),
(b) 20 to 60 wt.-%, preferably 30 to 55 wt.-% and particularly preferably 33 to 55 wt.-% of at least one urethane di[meth]acrylate telechel of Formula (II),
(c) 0 to 30 wt.-%, preferably 0 to 20 wt.-% and particularly preferably 0 wt.-% of further di(meth)acrylate monomers,
(d) 2 to 12 wt.-%, preferably 2 to 10 wt.-% and particularly preferably 3 to 8 wt.-% of at least one ABA or AB block copolymer,
(e) 0.1 to 5.0 wt.-%, preferably 0.2 to 4 wt.-% and particularly preferably 0.3 to 3.0 wt.-% of at least one photoinitiator, (f) 0 to 15 wt.-%, preferably 0 to 5 wt.-% and particularly preferably 0 wt.-% of core-shell polymer particles,
(g) 0 to 20 wt.-%, preferably 0 to 15 wt.-% and particularly preferably 0 to 10 wt.-% of filler,
(h) 0 to 1.0 wt.-%, preferably 0 to 0.7 and particularly preferably 0 to 0.5 wt.-% of UV absorber,
(i) 0 to 0.5 wt.-%, preferably 0 to 0.1 wt.-% and particularly preferably 0 to 0.05 wt.-% of optical brightener and
(j) 0 to 15 wt.-%, preferably 0 to 10 wt.-% and particularly preferably 0.02 to 5 wt.-% of further additives.

Unless otherwise stated, all percentages by weight herein relate to the total mass of the dental material.

Dental materials which contain
(a) 40 to 61 wt.-% of 2-phenoxyethyl (meth)acrylate, 2-(o-biphenyloxy)ethyl (meth)acrylate, 2-hydroxy-3-phenoxypropyl (meth)acrylate, 2-[(benzyloxycarbonyl)amino]ethyl (meth)acrylate, 1-phenoxypropan-2-yl (meth)acrylate, 2-(benzyloxy)-ethyl (meth)acrylate, 2-(methacryloyloxy)ethyl (meth)acrylate, 3-phenoxybenzyl (meth)acrylate, phenoxypropyl (meth)acrylate, 2-benzyloxyethyl (meth)acrylate, 2-benzoyloxyethyl (meth)acrylate, 2-(meth)acryloyloxybenzoic acid methyl ester, 2-phenylethyl (meth)acrylate, tricyclodecane (meth)acrylate, tricyclodecane methyl (meth) acrylate and/or 2-(p-cumylphenoxy)ethyl methacrylate,
(b) 33 to 55 wt.-% of at least one urethane di(meth)acrylate telechel with a number-average molar mass of 750-2000 g/mol and with at least 4 urethane groups, prepared by reacting 1 mol ethoxylated or propoxylated bisphenol A, decanediol or dodecanediol with 2 mol isophorone diisocyanate (IPDI) and then reacting with 2 mol 2-hydroxyethyl methacrylate (HEMA) or hydroxypropyl methacrylate (HPMA),
(c) 0 wt.-% of further di(meth)acrylate monomers,
(d) 2 to 10 wt.-% of at least one ABA or AB block copolymer, wherein the A block is made up of oligomeric polycaprolactone, poly(2,6-dimethyl-1,4-phenylene oxide), poly(ethylene oxide), poly(propylene oxide) or poly(meth)acrylate building blocks and the B block is made up of poly(dimethylsiloxane), poly(isoprene), poly(vinyl acetate), poly(isobutene), cis-poly(butadiene) or poly(ethylene) building blocks,
(e) 0% of core-shell polymers,
(f) 0.1 to 5.0 wt.-% of at least one photoinitiator and
(g) 0.2 to 5 wt.-% of one or more further additives,
are particularly preferred according to the invention.

The dental materials according to the invention are characterized in that they have a high fracture toughness and fracture work and at the same time a good flexural strength and a relatively high modulus of elasticity, measured at 37° C. in water, which corresponds to oral conditions. The materials also have a high transparency and a low viscosity. It is particularly advantageous that the dental materials still have a high transparency and a low intrinsic colour even after curing.

In contrast thereto, the core-shell polymers used in the state of the art as impact modifiers usually bring about a more or less pronounced reduction in the transparency, which is disadvantageous for additive processes. It was found that the block copolymers (d) make it possible to improve the fracture toughness, but in comparison with core-shell polymers only result in a relatively small impairment of the transparency. Since, moreover, a much smaller quantity of block copolymers (d) is necessary to achieve the desired fracture toughness compared with core-shell polymers, the block copolymers (d) make it possible to produce materials with high transparency, which are eminently suitable for additive processes.

The fracture toughness-increasing action of the block polymers (d) is particularly pronounced when the crosslinking density $v_c$ of the materials lies in a range of from 300 to 5000 mol/m$^3$ and preferably 400 to 3000 mol/m$^3$. Although a higher crosslinking density brings about an increase in the flexural strength and the modulus of elasticity, it leads to a lower fracture strength of the polymers. A reduction in the crosslinking density increases the fracture toughness, but has a disadvantageous effect on the flexural strength and the modulus of elasticity.

A crosslinking density in the preferred range is achieved through the use of urethane di(meth)acrylate telechels (b) with a number-average molar mass of from 750 to 2000 g/mol as crosslinker, wherein the crosslinking density can be finely adjusted through the addition of small quantities of monomeric di(meth)acrylates.

According to the invention, materials with a transparency ≥60%, preferably ≥70% and quite particularly preferably ≥80%, and a viscosity ≤10.0 Pa·s, preferably ≤5.0 Pa·s, are particularly preferred. The transparency is measured in accordance with the ISO 10526:1999 standard, as described above. The viscosity is determined using a cone-plate viscometer in the manner described above.

After curing, the materials according to the invention have a fracture toughness $K_{max}$ of greater than 1.1 MPa·m$^{1/2}$, preferably greater than 1.2 MPa·m$^{1/2}$, particularly preferably greater than 1.4 MPa·m$^{1/2}$ as well as a fracture work FW greater than 250 J/m$^2$, preferably greater than 300 J/m$^2$, particularly preferably greater than 400 J/m$^2$. Workpieces which are produced from these materials thus withstand, to a high degree, deformations without fracturing. A high transparency in combination with a high fracture work cannot be achieved with core-shell polymers.

The determination of the fracture toughness $K_{max}$ and the fracture work FW is effected in accordance with ISO 20795-1:2013 in the 3-point flexural test with a support span of 32 mm. The determination of $K_{max}$ and FW is based on the theoretical principles of the stress intensity factor $K_{1C}$. The fracture toughness $K_{max}$ is the highest factor of the stress intensity, which is also called the stress intensity factor at highest load, and is calculated as follows:

$$K_{max} = \left(\frac{P_{max} \cdot S}{B \cdot W^{3/2}}\right) \cdot f(x) \cdot 0.031 \ MPa \cdot m^{1/2}, \text{ where}$$

$$f(x) = 3 \cdot \sqrt{x} \ \frac{1.99 - x(1-x) \cdot (2.15 - 3.93x + 2.7x^2)}{2(1+2x) \cdot (1-x)^{\frac{3}{2}}},$$

$$\text{wherein } x = \frac{a}{W}$$

and W is the test piece height (=8 mm), B is the test piece thickness (=4 mm), a is the crack length (=3 mm+crack depth with razor blade), S is the support span (=32 mm) and $P_{max}$ is the maximum pressure in the test.

The fracture work FW (fracture work, total fracture work) is calculated in the following manner:

$$FW = \frac{U}{2B(W-a)} \cdot 100 \ J/m^2$$

wherein U is the total energy which is required to fracture the sample (integral of the load/distance graph) and which is needed to create the two new fracture planes B(W−a). This parameter describes the resistance of the material to crack propagation.

After curing, the materials according to the invention have a good flexural strength and a relatively good flexural modulus as well as a good fracture toughness and a high fracture work. Shaped parts which are obtained by curing the materials according to the invention have a high stiffness and oppose a deformation with a high level of resistance without fracturing. Materials which have a flexural strength after curing, determined in accordance with ISO20795-1:2013, of at least 40 MPa, particularly preferably 50 MPa or more and quite particularly preferably of 60 MPa or more are preferred. Moreover, the cured materials preferably have a flexural modulus, determined in accordance with ISO20795-1:2013, of at least 1000 MPa, preferably of 1300 MPa or more, particularly preferably of 1500 MPa or more, quite particularly preferably 2000 MPa or more and most preferably of 2500 MPa. In addition, the materials have a fracture toughness $K_{max}$ of 1.1 MPa·m$^{1/2}$ or more, preferably 1.2 MPa·m$^{1/2}$ or more, particularly preferably 1.4 MPa·m$^{112}$ or more as well as a fracture work FW of 250 J/m$^2$ or more, preferably 300 J/m$^2$ or more, particularly preferably 400 J/m$^2$ or more. Therefore, materials with a flexural strength of from 60 to 100 MPa, a flexural modulus of from 2000 to 2500 MPa, a fracture toughness $K_{max}$ of from 1.4 to 2.5 MPa·m$^{1/2}$ and a fracture work FW of from 400 to 800 J/m$^2$ are particularly preferred.

According to a particularly preferred embodiment of the invention, after curing the materials have a flexural strength of 50 MPa or more, measured according to ISO20795-1:2013, and a fracture work of 250 J/m$^2$ or more and a $K_{max}$ value (highest factor of the stress intensity) of at least 1.2 MPa·m$^{0.5}$.

Due to the above properties, the materials according to the invention are eminently suitable for use as a dental material, e.g. as a prosthetic material or veneering material, and in particular for the production or repair of dental shaped parts, such as e.g. dental restorations, prostheses, artificial teeth, inlays, onlays, crowns, bridges, drilling templates, splints (bite splints), try-in bodies and orthodontic appliances, such as e.g. plastic correction splints, so-called aligners and positioners. The named shaped parts are also a subject of the invention. The dental materials according to the invention are preferably used extraorally, i.e. non-therapeutically.

A further subject of the present invention is a process for the production of dental shaped parts, in particular for the production of the above-named dental shaped parts, in which a composition according to the invention is cured with the aid of light in order to give the dental shaped part. The production or repair of dental shaped parts is preferably effected extraorally, particularly preferably by an additive process, quite particularly preferably by 3D printing or a lithography-based process, such as e.g. stereolithography.

The stereolithographic production of shaped parts is preferably effected by creating a virtual image of the tooth situation by direct or indirect digitization of the tooth to be restored or of the teeth to be restored on a computer, then constructing a model of the dental restoration or prosthesis on the computer on the basis of this image and subsequently producing this model by additive stereolithographic manufacturing.

Once the virtual model of the dental workpiece to be produced has been created, the composition according to the invention is polymerized by selective light irradiation. The dental restoration or prosthesis is preferably constructed in layers by polymerizing a plurality of thin layers with the desired cross section one after another. After the layered construction of the restoration or prosthesis, excess residual resin is preferably removed. This can be effected by suitable mechanical processes (e.g. centrifuging or sandblasting) or by treatment with a suitable solvent, such as e.g. an alcohol, such as ethanol or isopropanol, a ketone, such as e.g. acetone, or an ester, such as e.g. ethyl acetate. A post-tempering is then preferably effected by heating or particularly preferably by irradiation of the workpiece with light of a suitable wavelength, such as e.g. irradiation with light with an intensity of e.g. 160 mW/cm$^2$ at 405 nm. When two photoinitiators are used, irradiation with two different wavelengths is advantageous. The workpiece is preferably heated to a temperature above 50° C. at the same time or in a subsequent step. The mechanical properties can be improved through the photochemical and/or thermal post-tempering.

The invention is explained in more detail in the following with reference to examples.

EXAMPLES

Example 1

Synthesis of 2-(2-biphenyloxy)-ethyl methacrylate (aromatic monomethacrylate)

1$^{st}$ Stage: 2-(2-biphenyl)-oxyethanol

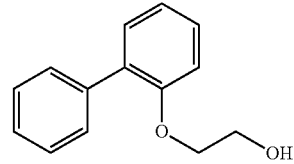 [SMILES: OCCOc1ccccc1-c1ccccc1]

In a double-jacketed reactor, 2.55 kg (15.0 mol) 2-phenylphenol, 0.12 kg (0.75 mol) potassium iodide and 0.17 kg (0.75 mol) benzyltriethylammonium chloride were added to a solution of 0.90 kg (22.5 mol) sodium hydroxide in 15.0 kg water. The solution was heated to 60° C. (internal temperature) and at the same time the dropwise addition of 1.81 kg (22.5 mol) 2-chloroethanol was begun. After the end of the addition, the batch was stirred at 60° C. for 48 h. For work-up, the batch was diluted with 6.0 l toluene, and after the phase separation the aqueous phase was extracted 2 more times with 3.0 l toluene each time. The combined toluene phases were washed 3 times with 4.0 l 1N sodium hydroxide solution each time, 3 times with 4.0 l 1N hydrochloric acid each time and 3 times with 3.0 l water each time. The toluene was distilled off in vacuo. After a recrystallization from toluene, 2.77 kg (86% yield) 2-(2-biphenyl)-oxyethanol was obtained as a colourless, crystalline solid (m.p.: 74-75° C.) with a purity of >99% (GC).

$^1$H-NMR (400 MHz, CDCl$_3$) δ(ppm)=1.86 (t, J=6.5 Hz, 1H, OH), 3.78-3.81 (m, 2H, HOCH$_2$), 4.04 (t, J=4.6 Hz, 2H, OCH$_2$), 6.98-7.08, 7.28-7.34, 7.38-7.42 and 7.50-7.52 (4 m, 2H, 3H, 2H, 2H, =CH).

$^{13}$C-NMR (100 MHz, CDCl$_3$) δ(ppm)=61.4 and 70.3 (OCH$_2$), 113.5 (C-6), 121.7 (C-4), 127.1, 128.7 and 131.0 (C-3, C-5, C-4'), 128.1 and 129.4 (C-2', C-3', C-5', C-6'), 131.5 and 138.4 (C-2, C-1'), 155.4 (C-1).

IR (diamond ATR): ν(cm$^{−1}$)=3329 (br, m, OH), 3056 (m, =CH), 2918 and 2866 (m, CH$_2$), 1596 and 1584 (m, C=C), 1502 and 1483 (s, aromatic compound), 1431 (s, CH$_2$), 1260 and 1077 (s, COC), 1054 (s, COH), 749, 730 and 700 (vs, =CH).

2$^{nd}$ Stage: 2-(2-biphenyloxy)-ethyl methacrylate

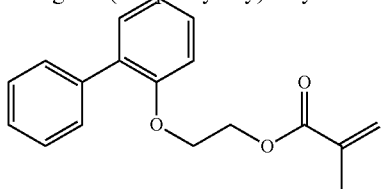

In a double-jacketed reactor, 0.75 kg (7.4 mol) triethylamine, 37.9 g (0.31 mol) 4-dimethylaminopyridine and 0.35 g 2,6-di-tert-butyl-4-methylphenol were added to a solution of 1.33 kg (6.2 mol) 2-(2-biphenyl)-oxyethanol in 13.0 l methylene chloride. A solution of 1.14 kg (7.4 mol) methacrylic acid anhydride was added dropwise at 0° C. (internal temperature) and stirred at this temperature for a further 2 h and at 20° C. for 20 h. The solution was then washed 3 times with 4.0 l 1N hydrochloric acid each time, 3 times with 4.0 l 1N sodium hydroxide solution each time and 3 times with 4.0 l water each time. The organic phase was stabilized with 0.09 g phenothiazine. After the solvent had been removed, 1.71 kg (98% yield) 2-(2-biphenyloxy)-ethyl methacrylate (BPOEMA) was obtained as a virtually colourless oil with a purity of 96.45% (GC).

$^1$H-NMR (400 MHz, CDCl$_3$) δ(ppm)=1.93 (s, 3H, CH$_3$), 4.19 and 4.41 (2 t, each J=4.8 Hz, each 2H, OCH$_2$), 5.55 and 6.08 (2 s, each 1H, =CH$_2$), 6.95-7.06, 7.26-7.30, 7.33-7.37 and 7.52-7.55 (4 m, 2H, 2H, 3H, 2H, =CH).

$^{13}$C-NMR (100 MHz, CDCl$_3$) δ(ppm)=18.3 (CH$_3$), 63.0 and 66.5 (OCH$_2$), 113.1 (C-6), 121.7 (C-4), 126.0 (C=CH$_2$), 126.9, 128.6, 131.1 (C-3, C-5, C-4'), 127.9 and 129.6 (C-2', C-3', C-5', C-6'), 131.3 and 138.3 (C-2, C-1'), 136.1 (C=CH$_2$), 155.4 (C-1), 167.2 (C=O). IR (diamond ATR): ν(cm$^{-1}$)=3027 (w, =CH), 2955 and 2900 (w, CH$_2$, CH$_3$), 1716 (vs, C=O), 1636 (m, C=C$_{methacryl}$), 1598 and 1584 (m, C=C$_{aromatic\ compound}$), 1504 and 1482 (m, s, aromatic compound), 1434 (5, CH$_2$, CH$_3$), 1261 and 1125 (5, COC$_{ether}$), 1157 (vs, COC$_{ester}$), 939 (s, =CH$_{methacryl}$), 751, 733 and 697 (vs, =CH$_{aromatic\ compound}$).

The rotational viscosity of BPOEMA was determined as η=0.01 Pa·s using an MCR rheometer (Anton Paar GmbH, Austria). The refractive index of BPOEMA was determined as n$_D^{20}$=1.5729 by means of an ABBE 5 refractometer (Bellingham+Stanley, UK). The density of BPOEMA was determined as 1.119 g/cm$^3$ by means of a flexural resonator density meter DS 7000 (Krüss). A polymerization shrinkage of only 7.4 vol.-% was determined for the monomer.

Example 2

Synthesis of Urethane Dimethacrylate Telechels According to the Invention

General Specification for Reacting Diols with Diisocyanates and HEMA End-Capping (1:2:2)

A mixture of 1 equivalent diol, 2 equivalents isophorone diisocyanate (IPDI) and 700 ppm Metatin 712 (relative to IPDI) was heated to 40° C. The diol dissolved completely and the mixture heated up to approx. 110° C. After the exothermicity had subsided, the mixture was stirred at 80° C. bath temperature for 1 h before 2 equivalents 2-hydroxyethyl methacrylate (HEMA, stabilized with 30 ppm (relative to 100% product) BHT) were added dropwise. After the exothermicity had subsided again, stirring was continued for a further 10 min at 90° C. The completeness of the reaction was checked by IR and NMR spectroscopy. The adducts were obtained as colourless, very highly viscous to brittle resins.

A. 1,10-Decanediol-IPDI-HEMA Adduct (1:2:2), Isomer Mixture (DMA Telechel 1, Molar Mass: 879.15 g/Mol)

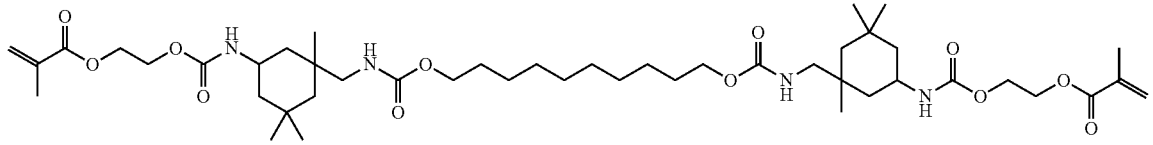 [SMILES: C=C(C)C(=O)OCCOC(=O)NC1CC(C)(C)CC(C)(CNC(=O)OCCCCCCCCCCOC(=O)NCC2(C)CC(NC(=O)OCCOC(=O)C(=C)C)CC(C)(C)C2)C1]

1,10-Decanediol was used as diol.

$^1$H NMR (400 MHz, CDCl$_3$): δ(ppm)=0.85-0.97, 1.01-1.06, 1.19-1.38 and 1.59-1.75 [4 m, 46H, (CH$_2$)$_8$, CH$_{2,\ cycl.}$, CH$_{3,\ cycl.}$), 2.03 (s, 6H, CH$_{3,\ methacryl}$), 2.81-2.98 and 3.20-3.33 (2 m, 4H, NCH$_2$), 3.65-3.88 [m, 2H, NCH], 3.98-4.11 (m, 4H, OCH$_2$(CH$_2$)$_8$), 4.26-4.40 (m, 8H, O(CH$_2$)$_2$O), 4.57-4.94 (m, 4H, NH), 5.60 and 6.14 (2 s, each 2H, =CH$_2$).

IR (diamond ATR): ν(cm$^{-1}$)=3341 (br, NH), 2927 and 2856 (m, C—H), 1695 (vs, C=O), 1638 (m, C=C), 1526 (s, NH), 1456 (m, CH$_2$, CH$_3$), 1366 (m, CH$_3$), 1236 (C—N), 1167 and 1039 (s, m, COC), 942 (m, =CH), 774 [m, (CH$_2$)$_8$].

B. Bisphenol A-IPDI-HEMA Adduct (1:2:2), Isomer Mixture (DMA Telechel 2, Molar Mass: 1049.31 g/mol)

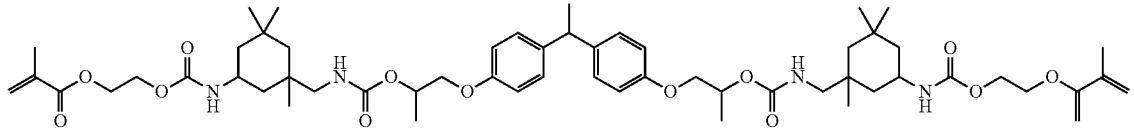 [SMILES: C=C(C)C(=C)OCCOC(=O)NC1CC(C)(C)CC(C)(CNC(=O)OC(C)COc2ccc(C(C)c3ccc(OCC(C)OC(=O)NCC4(C)CC(NC(=O)OCCOC(=O)C(=C)C)CC(C)(C)C4)cc3)cc2)C1]

A bisphenol A derivative with pendant isopropoxy groups in accordance with the following formula was used as diol:

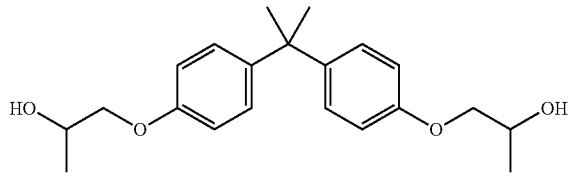 [SMILES: CC(O)COc1ccc(C(C)(C)c2ccc(OCC(C)O)cc2)cc1]

$^1$H NMR (400 MHz, CDCl$_3$): δ(ppm)=0.86-1.06, 1.18-1.21, 1.29-1.40 and 1.62-1.75 [4 m, 42H, CH$_{2, cycl.}$, CH$_3$], 1.95 (s, 6H, CH$_{3, methacryl}$), 2.87-2.99 and 3.19-3.36 (2 m, 4H, NCH$_2$), 3.67-3.88 [m, 2H, NCH], 3.91-4.03 and 4.09-4.22 (2 m, 4H, OCH$_2$CH), 4.26-4.40 and 4.50-5.18 (2 m, 14H, O(CH$_2$)$_2$O, OCH$_2$CH, NH), 5.59 and 6.15 (2 s, each 2H, =CH$_2$), 6.80 and 7.12 (2 d, each 4H, =CH).

IR (diamond ATR): ν(cm$^{-1}$)=3341 (br, NH), 2955 and 2860 (m, C—H), 1705 (vs, C=O), 1640 (w, C=C), 1608 (w, aromatic compound), 1507 (s, NH), 1456 (m, CH$_2$, CH$_3$), 1385 (m, CH$_3$), 1231 (C—N), 1155 and 1043 (s, m, COC), 941 (m, =CH), 829 (m, =CH$_{aromatic\ compound}$).

Example 3

Synthesis of PCL(1600)-b-PDMS(3200)-b-PCL(1600) Block Copolymer (PO-277)

1$^{st}$ Stage: tetramethylammonium 3-aminopropyl dimethylsilanoate

In a protective gas atmosphere, a mixture of 1,3-bis(3-aminopropyl)tetramethyldisiloxane (2.49 g, 10.0 mmol) and tetramethylammonium hydroxide pentahydrate (3.62 g, 20 mmol) in tetrahydrofuran (THF; 10 ml) was heated at reflux for 3 h. The solvent was distilled off and the residue was heated to 50° C. in a fine vacuum. The yellowish residue was recrystallized from THF (20 ml). 3.17 g (15.4 mmol; 77%) of a white solid was obtained.

$^1$H-NMR (CDCl$_3$, 400 MHz): δ=3.16 (s, 12H; N$^+$—CH$_3$), 2.37 (t, 2H; J=7.1 Hz; N—CH$_2$), 1.28 (m, 2H; CH$_2$), 0.14 (m, 2H; Si—CH$_2$), −0.33 (s, 6H; Si—CH$_3$).

2$^{nd}$ Stage: polydimethylsiloxane-αω-dipropyl-3-amine: PDMS(3200)

In a protective gas atmosphere, a mixture of 1,3-bis(3-aminopropyl)tetramethyldisiloxane (4.98 g, 20.0 mmol) and octamethylcyclotetrasiloxane (12.00 g, 40 mmol) was heated to 80° C. Tetramethylammonium 3-aminopropyl dimethylsilanoate (20 mg) was added and stirring was continued at 80° C. After 30 min, octamethylcyclotetrasiloxane saturated with argon (56.00 g, 0.192 mol) was slowly added dropwise. The reaction mixture was stirred at 80° C. for a further 18 h and then heated to 150° C. for 30 min to break down the catalyst. Volatile components were then removed in a fine vacuum. 65.30 g (88%) of a colourless oil was obtained.

$^1$H-NMR (CDCl$_3$, 400 MHz): δ=2.64 (t, 4H; J=7.0 Hz; N—CH$_2$), 1.43 (m, 4H; CH$_2$), 0.51 (m, 4H; Si—CH$_2$), 0.05 (s, 250H; Si—CH$_3$).

3$^{rd}$ Stage: PCL(1600)-b-PDMS(3200)-b-PCL(1600) Block Copolymer

A mixture of PDMS(3200) (20.00 g) and ε-caprolactone (20.40 g) was heated to 80° C. After 1 h, tin bis(2-ethylhexanoate) (10 mg) was added and the bath temperature increased to 130° C. in stages over 30 min. The now clear reaction mixture was stirred at 130° C. for a further 5 h.

Then, volatile components were distilled off in a fine vacuum. 39.50 g (98%) of the block copolymer was obtained as a waxy, slightly yellowish solid.

$^1$H-NMR (CDCl$_3$, 400 MHz): δ=3.99 (t, 55H; J=6.8 Hz; O—CH$_2$), 3.57 (t, 4H; J=6.8 Hz; HO—CH$_2$), 3.15 (q, 4H; J=6.8 Hz; N—CH$_2$), 2.24 (t, 55H; J=7.5 Hz; C(O)—CH$_2$), 2.10 (t, 4H; J=7.5 Hz; N—CH$_2$), 1.58 (m, 118H; CH$_2$), 1.32 (m, 59H; CH$_2$), 0.46 (m, 4H; Si—CH$_2$), 0.02 (s, 250H; Si—CH$_3$).

Example 4

Synthesis of PMMA(1200)-b-PDMS(3200)-b-PMMA(1200) Block Copolymer

1$^{st}$ Stage: α,ω-(2-bromoisobutyrylaminopropyl)- poly(dimethylsiloxane)

α-Bromoisobutyric acid bromide (1.44 g; 6.24 mmol) was added dropwise at 0° C. to a solution of PDMS(3200) (6.66 g; 2.08 mmol) and triethylamine (0.84 g; 8.44 mmol) dissolved in THF (100 ml). The reaction mixture was stirred for 2 h with ice-cooling and at ambient temperature for 18 h. The suspension was filtered and the filtrate was concentrated on a rotary evaporator. The colourless oil was dissolved in dichloromethane (100 ml) and washed with saturated aqueous Na$_2$CO$_3$ solution (2 times 50 ml), hydrochloric acid (0.2N, 2 times 50 ml) and saturated aqueous NaCl solution (100 ml), dried over anhydrous sodium sulfate, filtered and concentrated on a rotary evaporator. Volatile components were removed in a fine vacuum. 6.32 g (1.81 mmol; 87%) of a slightly yellowish liquid was obtained.

$^1$H-NMR (CDCl$_3$, 400 MHz): δ=3.22 (m, 4H; N—CH$_2$), 1.92 (s, 12H; C—CH$_3$), 1.54 (m, 4H; CH$_2$), 0.53 (m, 4H; Si—CH$_2$), 0.05 (s, 258H; Si—CH$_3$).

2$^{nd}$ Stage: PMMA(1200)-b-PDMS(3200)-b-PMMA(1200) Block Copolymer

Under inert gas conditions, toluene (50 ml) was added to α,ω-(2-bromoisobutyrylaminopropyl)-poly(dimethylsiloxane) (6.22 g; 1.78 mmol), copper(I) chloride (0.35 g; 3.56 mmol) and N,N,N',N'',N''-pentamethyldiethylenetriamine (0.62 g; 3.56 mmol) and the solution was degassed. Methacrylic acid methyl ester (7.78 g; 77.7 mmol) was added. The solution was stirred at ambient temperature for 30 min and then heated to 90° C. for 20 h. After cooling, the solution was filtered over neutral aluminium oxide. The filtrate was concentrated on a rotary evaporator. The residue was dissolved in dichloromethane and filtered over silica gel. The filtrate was concentrated on a rotary evaporator and the residue was dried in a fine vacuum. 8.77 g (1.49 mmol; 84%) of the block copolymer was obtained as a yellowish solid.

$^1$H-NMR (CDCl$_3$, 400 MHz): δ=3.53 (s, 72H; O—CH$_3$), 3.28-3.03 (m, 4H; N—CH$_2$), 2.20-1.12 (m, 64H; C—CH$_3$, CH$_2$), 1.13-0.63 (m 72H, CH$_3$), 0.55-0.40 (m, 4H; Si—CH$_2$), 0.0 (s, 252H, Si—CH$_3$).

Example 5

Synthesis of PCL(2500)-b-PDMS(3200)-b-PCL(2500) Block Copolymer

A mixture of PDMS(3200) (20.00 g) and ε-caprolactone (30.60 g) was heated to 80° C. After 1 h, tin bis(2-ethylhexanoate) (10 mg) was added and the bath temperature was increased to 130° C. in stages over 30 min. The now clear reaction mixture was stirred at 130° C. for a further 5 h. Then, volatile components were distilled off in a fine vacuum. 49.00 g (97%) of a waxy, slightly yellowish solid was obtained.

$^1$H-NMR (CDCl$_3$, 400 MHz): δ=3.99 (t, 86H; J=6.8 Hz; O—CH$_2$), 3.57 (t, 4H; J=6.8 Hz; HO—CH$_2$), 3.15 (q, 4H; J=6.8 Hz; N—CH$_2$), 2.24 (t, 86H; J=7.5 Hz; C(O)—CH$_2$), 2.10 (t, 4H; J=7.5 Hz; N—CH$_2$), 1.60-1.54 (m, 180H; CH$_2$), 1.34-1.29 (m, 90H; CH$_2$), 0.51-0.40 (m, 4H; Si—CH$_2$), 0.02 (s, 250H; Si—CH$_3$).

Example 6

Synthesis of PCL(3200)-b-PDMS(3200)-b-PCL(3200) Block Copolymer

A mixture of PDMS(3200) (15.00 g) and ε-caprolactone (30.60 g) was heated to 80° C. After 1 h, tin bis(2-ethylhexanoate) (10 mg) was added and the bath temperature was increased to 130° C. in stages over 30 min. The now clear reaction mixture was stirred at 130° C. for a further 5 h. Then, volatile components were distilled off in a fine vacuum. 44.20 g (97%) of a waxy, slightly yellowish solid was obtained.

$^1$H-NMR (CDCl$_3$, 400 MHz): δ=3.99 (t, 106H; J=6.8 Hz; O—CH$_2$), 3.57 (t, 4H; J=6.8 Hz; HO—CH$_2$), 3.15 (q, 4H; J=6.8 Hz; N—CH$_2$), 2.24 (t, 106H; J=7.5 Hz; C(O)—CH$_2$), 2.10 (t, 4H; J=7.5 Hz; N—CH$_2$), 1.60-1.54 (m, 220H; CH$_2$), 1.34-1.29 (m, 110H; CH$_2$), 0.51-0.40 (m, 4H; Si—CH$_2$), 0.02 (s, 250H; Si—CH$_3$).

Example 7

Preparation of Polymerization and SL Resins

The components listed in Table 1 were homogeneously mixed with each other in the stated quantities. For this, all solid components (block copolymer or core-shell particles, photoinitiator) were dissolved in the monomers with stirring in a planetary mixer or Speedmixer, optionally also with heating to 50° C. The urethane dimethacrylate telechels were then added and stirring continued until a homogeneous mixture was achieved. The block copolymers could be incorporated into the mixtures without problems. For the incorporation of core-shell particles, homogenization was additionally carried out for 30 minutes at a rotational speed of 3000 rpm by means of a rotor-stator mixer (Ultra-Turrax T-25). The mixtures were then deaerated in a planetary mixer.

Test pieces were produced in a bottom-up process with formulations no. 5 and no. 6 using a stereolithographic printer (PrograPrint PRS, from Ivoclar Vivadent AG, Schaan, Liechtenstein). The printer exposed the samples using the DLP technique with a wavelength of 388 nm, a power of 10 mW/cm$^2$ and a pixel size of 50 μm in a layered construction. The layer thickness was 100 μm in each case. Adhering residual resin was removed using isopropanol. For this, the test pieces were cleaned twice (first bath 10 min, second bath 5 min) in fresh isopropanol with stirring together with the build platform (PrograPrint Stage) using a PrograPrint Clean device (from Ivoclar Vivadent AG, Schaan, Liechtenstein) and immediately following this blow-dried with compressed air. Then, the test pieces were post-tempered by exposure for 90 s to light with a wavelength of 405 nm. This was effected by means of a PrograPrint Cure device (from Ivoclar Vivadent AG, Schaan, Liechtenstein; software: ProArt Print Splint, 2020). The test pieces were then detached from the build platform.

Test pieces were prepared in metal moulds with the remaining compositions from Table 1 and irradiated on both sides with a dental light source (PrograPrint Cure, from Ivoclar Vivadent AG, Schaan, Liechtenstein; software: ProArt Print Splint, 2020) and thus cured.

The further machining and storage of the test pieces was effected in accordance with the relevant provisions of the specifications named below. The flexural strength (FS) and the flexural modulus of elasticity (FM) were determined according to the ISO standard ISO-4049 (Dentistry—Polymer-based filling, restorative and luting materials). For this, the test pieces were, beforehand, either stored dry at room temperature for 24 h or in water at 37° C. for 24 h. In addition, the flexural strength and the flexural modulus were measured according to the ISO 20795-1:2013 standard (Dentistry—Base polymers—Part 1: Denture base polymers). Accordingly, before the measurement the test pieces were stored in deionized water at 37° C. for 50 h and then the measurement was carried out in a thermostatically controlled tank under water at 37° C. The determination of the fracture toughness K$_{max}$ and of the fracture work FW was effected in accordance with ISO 20795-1:2013. The results of the measurements are given in Table 2.

Formulations no. 1 and no. 10 are reference examples, which contain neither core-shell polymers nor block copolymers. Although these reference examples have a good flexural strength and a good flexural modulus, the values for the fracture toughness and the fracture work are poor and unusable for the intended stereolithographic applications. Examples no. 3, no. 4 and no. 14 in each case contain core-shell polymer particles. In all cases, the addition of the particles brings about an improvement in the fracture toughness (K$_{max}$ and fracture work FW).

In Example no. 14, 5 wt.-% core-shell particles was added to formulation no. 10. The addition of the core-shell polymer brings about not only an improvement in the fracture toughness but also a significant deterioration in the transparency. In Examples no. 12, no. 13 and no. 15, in each case 5 wt.-% of a block copolymer was added as impact modifier in place of the core-shell particles. Table 2 shows that in all cases the block copolymers give a much greater improvement in the fracture toughness than the core-shell particles, but result in only a comparatively small deterioration in the transparency. Example no. 11 shows that the addition of 3 wt.-% of a block copolymer is sufficient to achieve a similar improvement in the fracture toughness to 5 wt.-% core-shell particles.

A comparison of Examples no. 2 and no. 3 shows that, here too, the addition of 3 wt.-% block copolymer gives approximately the same improvement in the fracture toughness as 5 wt.-% core-shell particles. Example no. 2 is characterized, compared with Example no. 3, by a higher transparency and confirms that the use of block copolymers makes it possible to produce materials with high fracture toughness and transparency.

A comparison of Examples no. 3 and no. 4 shows that, although it is possible to further improve the fracture toughness by increasing the quantity of core-shell particles from 5 to 10 wt.-%, this is associated with an increasing deterioration in the transparency.

TABLE 1

Composition of the polymerization and SL resins (data in wt.-%)

| Batch | Dimethacrylate V380[a)] | Urethane dimethacrylate telechel Ex. 2a | Urethane dimethacrylate telechel Ex. 2b | Mono(meth)-acrylate Ex. 1 | Mono(meth)-acrylate 2-PEMA[b)] | Mono(meth)-acrylate TCDA[c)] | Photo-initiator TPO[d)] | Core-shell particles MZ110[e)] | Block co-polymer Ex. 5 | Block co-polymer Ex. 6 | Block co-polymer PCL-b-PDMS-b-PCL[f)] |
|---|---|---|---|---|---|---|---|---|---|---|---|
| No. 1*) |  | 49.5 |  |  | 49.5 |  | 1.0 |  |  |  |  |
| No. 2 |  | 48.0 |  |  | 48.0 |  | 1.0 |  |  |  | 3.0 |
| No. 3*) |  | 47.0 |  |  | 47.0 |  | 1.0 | 5.0 |  |  |  |
| No. 4*) |  | 44.5 |  |  | 44.5 |  | 1.0 | 10.0 |  |  |  |
| No. 5 |  | 47.0 |  |  |  | 47.0 | 1.0 |  |  |  | 5.0 |
| No. 6 |  | 45.8 |  |  |  | 45.8 | 1.0 |  |  |  | 7.5 |
| No. 7 |  | 48.0 |  | 19.0 | 29.0 |  | 1.0 |  |  |  | 3.0 |
| No. 8 |  | 47.0 |  | 19.0 | 28.0 |  | 1.0 |  |  |  | 5.0 |
| No. 9 | 9.6 | 38.4 |  |  | 48.0 |  | 1.0 |  |  |  | 3.0 |
| No. 10*) |  |  | 49.5 |  | 49.5 |  | 1.0 |  |  |  |  |
| No. 11 |  |  | 48.0 |  | 48.0 |  | 1.0 |  |  |  | 3.0 |
| No. 12 |  |  | 47.0 |  | 47.0 |  | 1.0 |  | 5.0 |  |  |
| No. 13 |  |  | 47.0 |  | 47.0 |  | 1.0 |  |  | 5.0 |  |
| No. 14*) |  |  | 47.0 |  | 47.0 |  | 1.0 | 5.0 |  |  |  |
| No. 15 |  |  | 47.0 |  | 47.0 |  | 1.0 |  |  |  | 5.0 |
| No. 16 |  |  | 33.0 |  | 61.0 |  | 1.0 |  |  |  | 5.0 |

*)comparison example
[a)]addition product of a mixture of 0.7 mol 2-hydroxyethyl methacrylate and 0.3 mol 2-hydroxypropyl methacrylate with 1 mol α,α,α',α'-tetramethyl-m-xylylene diisocyanate
[b)]2-phenoxyethyl methacrylate
[c)]tricyclodecane methyl acrylate
[d)]diphenyl(2,4,6-trimethylbenzoyl)phenylphosphine oxide (BASF)
[e)]core-shell polymer particles MZ110 (Kaneka)
[f)]PCL-b-PDMS-b-PCL block copolymer, the molar mass of the PDMS blocks is 3200 g/mol and the molar mass of the PCL blocks is 1600 g/mol

TABLE 2

Properties of the cured materials

| Batch | Viscosity[1)] η [Pa·s] | Flexural strength and modulus[5)] dry ISO4049 FS [MPa] | Flexural strength and modulus[5)] dry ISO4049 FM [MPa] | Flexural strength and modulus[6)] in water ISO4049 FS [MPa] | Flexural strength and modulus[6)] in water ISO4049 FM [MPa] | Flexural strength and modulus[7)] ISO20795-2 FS [MPa] | Flexural strength and modulus[7)] ISO20795-2 FM [MPa] | Fracture toughness ISO20795-2 $K_{max}$ [MPa·m$^{1/2}$] | Fracture toughness ISO20795-2 FW [J/m$^2$] | Glass transition temperature[3)] $T_G$ [°C] | Network density[4)] $v_c$ [mol/m$^3$] | Transparency[2)] [%] |
|---|---|---|---|---|---|---|---|---|---|---|---|---|
| No. 1*) | 1.2 | 128.6 | 3157 | 108.3 | 2642 | 86.7 | 2499 | 0.897 | 118 | 85.8 | 1365 | 88.6 |
| No. 2 | 1.5 | 89.4 | 2430 | 78.7 | 2208 | 71.4 | 2090 | 1.703 | 349 | 89.3 | 1660 | 81.0 |
| No. 3*) | 2.0 | 80.9 | 2307 | 86.5 | 2382 | 77.6 | 2077 | 1.732 | 370 | n.d. | n.d. | 76.1 |
| No. 4*) | n.d. | 106.5 | 2740 | 96.1 | 2451 | 56.2 | 1697 | 2.060 | 657 | n.d. | n.d. | 65.0 |
| No. 5 | n.d. | n.d. | n.d. | n.d. | n.d. | 59.1 | 1547 | 1.607 | 476 | n.d. | n.d. | n.d. |
| No. 6 | n.d. | n.d. | n.d. | n.d. | n.d. | 41.9 | 1036 | 1.604 | 616 | n.d. | n.d. | n.d. |
| No. 7 | 3.3 | 101.5 | 2729 | 87.9 | 2605 | 85.9 | 2553 | 1.610 | 287 | n.d. | n.d. | n.d. |
| No. 8 | 3.5 | 88.3 | 2424 | 86.9 | 2370 | 74.5 | 2148 | 2.082 | 577 | n.d. | n.d. | n.d. |
| No. 9 | 0.9 | 97.1 | 2753 | 88.0 | 2591 | 77.8 | 2273 | 1.481 | 255 | n.d. | n.d. | n.d. |
| No. 10*) | 4.2 | 117.2 | 3325 | 113.0 | 3103 | 85.2 | 3115 | 0.859 | 93 | 98.4 | 1060 | 90.9 |
| No. 11 | 4.4 | 100.5 | 3110 | 96.3 | 2950 | 88.5 | 2726 | 1.801 | 326 | n.d. | n.d. | 85.0 |
| No. 12 | 4.2 | 112.9 | 3221 | 104.7 | 2919 | 88.6 | 2507 | 2.068 | 489 | n.d. | n.d. | 88.2 |
| No. 13 | 4.8 | 109.1 | 3230 | 104.3 | 2855 | 88.5 | 2624 | 2.146 | 546 | n.d. | n.d. | 88.7 |
| No. 14*) | 3.7 | 105.9 | 3105 | 103.6 | 3170 | 65.1 | 2990 | 1.680 | 296 | n.d. | n.d. | 59.5 |
| No. 15 | 4.6 | 96.4 | 2858 | 96.3 | 2840 | 69.2 | 2192 | 2.010 | 613 | n.d. | n.d. | 83.0 |
| No. 16 | 4.1 | 107.1 | 3382 | 75.7 | 2381 | 62.8 | 1993 | 1.933 | 643 | n.d. | n.d. | 87.5 |

*)comparison example
n.d. not determined
[1)]rotational viscosity, determined using an Anton Paar model MCR 302 viscometer with a CP25-2 cone-plate measuring system and a measuring gap of 53 μm in rotation at a shear rate of 100/s at 25° C.
[2)]determined using a Konika-Minolta model CM-5 spectrophotometer on 1 mm-thick test pieces polished to high gloss in transmission (D65)
[3)]storage and loss modulus of a test piece (25 × 5 × 1 mm, clamped lengthways) were determined between 25° C. and 250° C. using an Anton Paar model MCR302 rheometer (frequency 1 Hz, deformation 0.05%, heating rate 2 K/min); $T_G$ corresponds to the maximum loss factor tan δ (ratio of loss modulus to storage modulus)
[4)]the network density was calculated according to the formula $v_c$ = G'/(RT), G' is the storage modulus at the temperature $T_G$ + 50 K; R is the generic gas constant; T is the temperature at $T_G$ + 50 K
[5)]flexural strength (FS) and flexural modulus (FM) measured in accordance with ISO4049 after dry storage at RT for 24 h
[6)]flexural strength (FS) and flexural modulus (FM) measured in accordance with ISO4049 after storage in water at 37° C. for 24 h
[7)]flexural strength (FS) and flexural modulus (FM) measured in accordance with ISO20795-2

The invention claimed is:

1. A radically polymerizable dental material, which comprises
at least one ABA or AB block copolymer (d),
at least one monofunctional, radically polymerizable monomer (a) and
at least one radically polymerizable urethane di(meth)acrylate telechel (b) with a number-average molar mass of from 750 to 2000 g/mol in accordance with general formula (II),

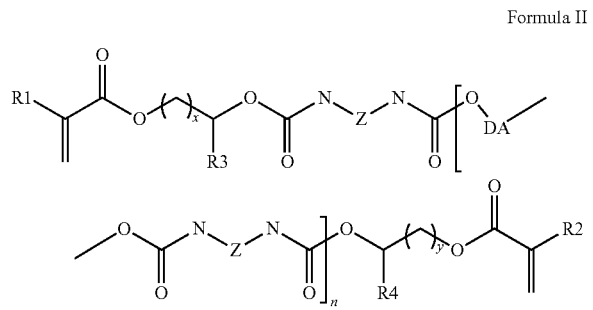

Formula II in which the variables have the following meanings:
$R^1$, $R^2$ independently of each other in each case H or methyl,
$R^3$, $R^4$ independently of each other in each case H or methyl,
x, y independently of each other in each case an integer from 1 to 11,
n 1, 2 or 3,
Z

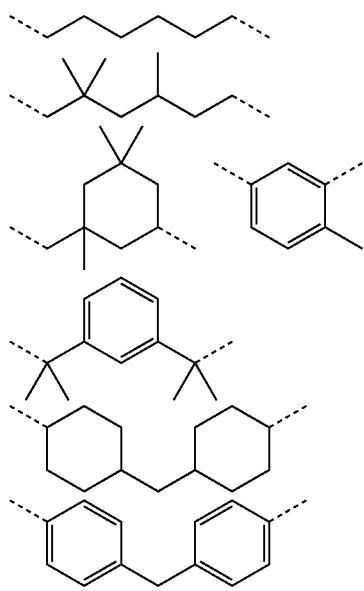

DA a structural element, which is derived from a diol HO-DA-OH by cleaving the hydrogen atoms from the hydroxyl groups, wherein the diol HO-DA-OH is selected from the following compounds: ethoxylated or propoxylated bisphenol A, o-diphenyl or p-diphenyl with 2 to 6 ethoxy or propoxy groups, $C_2$-$C_{18}$ alkanediols, which can contain 1 to 4 O or S atoms in the carbon chain, ethoxylated or propoxylated bisphenol A with 2, 3 or 4 ethoxy or propoxy groups, hexane-1,6-diol, octane-1,8-diol, nonane-1,9-diol, decane-1,10-diol, undecanediol or dodecane-1,12-diol, tetra- or pentaethylene glycol, cyclic or polycyclic aliphatic diols, cyclohexanediol, norbornanediol, tricyclodecanediol and tricyclodecanedimethanol (octahydro-4,7-methano-1H-indenedimethanol).

2. The radically polymerizable dental material according to claim 1, which comprises
(a) 30 to 70 wt.-% of at least one aromatic, bicyclic or tricyclic mono(meth)acrylate,
(b) 20 to 60 wt.-% of at least one urethane di(meth)acrylate telechel with a number-average molar mass of from 750 to 2000 g/mol,
(c) 0 to 30 wt.-% of di(meth)acrylate monomer(s),
(d) 1 to 12 wt.-% of at least one ABA and/or AB block copolymer, wherein the A block or blocks are homogeneously miscible with the mixture of components (a) to (c) and the B block is not homogeneously miscible with the mixture of components (a) to (c), and
(e) 0.1 to 5.0 wt.-% of at least one initiator for the radical polymerization,
in each case relative to the total mass of the material.

3. The radically polymerizable dental material according to claim 1, which comprises as component (a) at least one aromatic, bicyclic or tricyclic monomethacrylate of Formula (I)

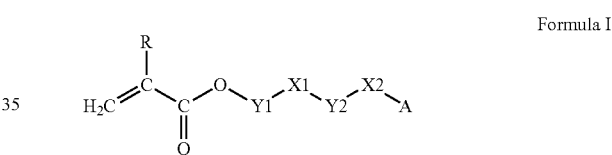

Formula I in which the variables have the following meanings:
A an aromatic group with 6 to 15 carbon atoms or a bicyclic or tricyclic aliphatic group with 7 to 10 carbon atoms, wherein A can be unsubstituted or substituted by one or more $C_1$-$C_5$ alkyl groups, $C_1$-$C_5$ alkoxy groups and/or chlorine atoms;
R hydrogen or methyl;
$X^1$, $X^2$ independently of each other is in each case absent or an ether, ester or urethane group, wherein $X^1$ is absent if $Y^1$ is absent and wherein $X^2$ is absent if $Y^2$ is absent;
$Y^1$, $Y^2$ independently of each other is in each case absent or a branched or linear aliphatic hydrocarbon radical with 1 to 10 carbon atoms, which can be interrupted by 1 to 3 oxygen atoms.

4. The radically polymerizable dental material according to claim 3, which comprises as component (a) 2-phenoxyethyl (meth)acrylate, 2-(o-biphenyloxy)ethyl (meth)acrylate, 2-hydroxy-3-phenoxypropyl (meth)acrylate, phenethyl (meth)acrylate, 2-[(benzyloxycarbonyl)-amino]-ethyl (meth)acrylate, 2-[(benzylcarbamoyl)-oxy]-ethyl (meth)acrylate, 1-phenoxypropan-2-yl (meth)acrylate and 2-(p-cumylphenoxy)-ethyl (meth)acrylate, 2-(benzyloxy)ethyl (meth)acrylate, 3-phenoxybenzyl (meth)acrylate, phenoxypropyl (meth)acrylate, 2-benzyloxyethyl (meth)acrylate, 2-benzoyloxyethyl (meth)acrylate, 2-(meth)acryloyloxybenzoic acid methyl ester, tricyclodecane (meth)acrylate, tricyclodecane methyl (meth)acrylate, 2-(p-cumylphenoxy) ethyl (meth)acrylate, 4,7,7-trimethylbicyclo[2.2.1]heptanyl (meth)acrylate, octahydro-1H-4,7-methanoinden-5-yl (meth)acrylate or a mixture thereof.

5. The radically polymerizable dental material according to claim 2, which comprises as component (d) at least one ABA and/or AB block copolymer, in which the A block is an oligomer which is made up of one or more of the following monomers: cyclic, aliphatic esters or ethers, arylene oxide, alkylene oxide, radically polymerizable monomers, α,β-unsaturated acids and α,β-unsaturated acid esters; and the B block is a polysiloxane oligomer and/or a polyvinyl oligomer and/or a polyalkene oligomer and/or a polydiene oligomer.

6. The radically polymerizable dental material according to claim 5, which comprises as component (d) at least one ABA and/or AB block copolymer, in which the A block is an oligomeric polycaprolactone (PCL), poly(2,6-dimethyl-1,4-phenylene oxide), poly(ethylene oxide), poly(propylene oxide) or poly(meth)acrylate building block and the B block is an oligomeric poly(dimethylsiloxane) (PDMS), poly(isoprene), poly(vinyl acetate), poly(isobutene), cis-poly(butadiene) or poly(ethylene) building block.

7. The radically polymerizable dental material according to claim 6, which comprises as component (d) at least one ABA triblock copolymer of the PCL-b-PDMS-b-PCL and/or PMMA-b-PDMS-b-PMMA type with a molar ratio of A:B of from 0.1 to 5 and with a molar mass of from 3 to 25 kDa, 4 to 20 kDa or 5 to 10 kDa.

8. The radically polymerizable dental material according to claim 2, which comprises as component (e) at least one photoinitiator, which is selected from benzophenone, benzoin or a derivative thereof, an α-diketone or a derivative thereof, 9,10-phenanthrenequinone, 1-phenyl-propane-1,2-dione, diacetyl or 4,4'-dichlorobenzil, camphorquinone (CQ), 2,2-dimethoxy-2-phenylacetophenone or an α-diketone in combination with an amine as reducing agent, 4-(dimethylamino)-benzoic acid ester (EDMAB), N,N-dimethylaminoethyl methacrylate, N,N-dimethyl-sym-xylidine or triethanolamine, monoacyltrialkyl-, diacyldialkyl-, tetraacylgermanium, a tetraacylstannane, benzoyltrimethylgermanium, dibenzoyldiethylgermanium, bis(4-methoxybenzoyl) diethylgermanium, tetrakis(2-methylbenzoyl)germane or tetrakis(mesitoyl)stannane or a mixture thereof, a Norrish type I photoinitiator comprising acetophenones, 2,2-diethoxy-1-phenylethanone, benzoin ethers, Irgacure 651 (benzil dimethyl ketal), hydroxyalkylphenylacetophenones, Irgacure 184 (1-hydroxycyclohexyl phenyl ketone), an acyl- or bisacylphosphine oxide, Irgacure TPO (2,4,6-trimethylbenzoyldiphenylphosphine oxide), Irgacure 819 (bis(2,4,6-trimethylbenzoyl) phenylphosphine oxide), 2-benzyl-2-(dimethylamino)-4'-morpholinobutyrophenone (Irgacure 369) and/or 1-butanone-2-(dimethylamino)-2-(4-methylphenyl) methyl-1-4-(4-morpholinyl)phenyl (Irgacure 379).

9. The radically polymerizable dental material according to claim 1, with the following composition:
(a) 30 to 70 wt.-% of at least one aromatic, bicyclic or tricyclic mono(meth)acrylate,
(b) 20 to 60 wt.-% of at least one urethane di(meth)acrylate telechel with a number-average molar mass of from 750 to 2000 g/mol,
(c) 0 to 30 wt.-% of di(meth)acrylate monomer(s),
(d) 1 to 12 wt.-% of at least one ABA or AB block copolymer,
(e) 0.1 to 5.0 wt.-% of at least one initiator for the radical polymerization,
(f) 0 to 15 wt.-% of core-shell polymer particles,
(g) 0 to 20 wt.-% % of filler,
(h) 0 to 1.0 wt.-% of UV absorber,
(i) 0 to 0.5 wt.-% of optical brightener and
(j) 0 to 15 wt.-% of further additives,
in each case relative to the total mass of the material.

10. Dental material according to claim 9, which comprises
(a) 40 to 61 wt.-% of 2-phenoxyethyl (meth)acrylate, 2-(o-biphenyloxy)ethyl (meth)acrylate, 2-hydroxy-3-phenoxypropyl (meth)acrylate, 2-[(benzyloxycarbonyl)amino]ethyl (meth)acrylate, 1-phenoxypropan-2-yl (meth)acrylate, 2-(benzyloxy)-ethyl (meth)acrylate, 2-(methacryloyloxy)ethyl (meth)acrylate, 3-phenoxybenzyl (meth)acrylate, phenoxypropyl (meth)acrylate, 2-benzyloxyethyl (meth)acrylate, 2-benzoyloxyethyl (meth)acrylate, 2-(meth)acryloyloxybenzoic acid methyl ester, 2-phenylethyl (meth)acrylate, tricyclodecane (meth)acrylate, tricyclodecane methyl (meth)acrylate and/or 2-(p-cumylphenoxy)ethyl methacrylate,
(b) 33 to 55 wt.-% of at least one urethane di(meth)acrylate telechel with a number-average molar mass of 750-2000 g/mol and with at least 4 urethane groups, prepared by reacting 1 mol ethoxylated or propoxylated bisphenol A, decanediol or dodecanediol with 2 mol isophorone diisocyanate (IPDI) and then reacting with 2 mol 2-hydroxyethyl methacrylate (HEMA) or hydroxypropyl methacrylate (HPMA),
(d) 2 to 10 wt.-% of at least one ABA or AB block copolymer, wherein the A block is made up of oligomeric polycaprolactone, poly(2,6-dimethyl-1,4-phenylene oxide), poly(ethylene oxide), poly(propylene oxide) or poly(meth)acrylate building blocks and the B block is made up of poly(dimethylsiloxane), poly(isoprene), poly(vinyl acetate), poly(isobutene), cis-poly (butadiene) or poly(ethylene) building blocks,
(e) 0.1 to 5.0 wt.-% of at least one photoinitiator and
(g) 0.2 to 5 wt.-% of one or more further additives,
in each case relative to the total mass of the material, and which is substantially free of di(meth)acrylate monomers and core-shell polymer particles.

11. The radically polymerizable dental material according to claim 1, which has a transparency of ≥60% and a viscosity of ≤10.0 Pas at 25° C.

12. The radically polymerizable dental material according to claim 1, which has a crosslinking density after curing of from 300 to 5000 mol/m$^3$.

* * * * *